United States Patent
Swoyer et al.

(10) Patent No.: US 8,911,438 B2
(45) Date of Patent: Dec. 16, 2014

(54) TUNA DEVICE WITH INTEGRATED SALINE RESERVOIR

(75) Inventors: John M. Swoyer, Andover, MN (US); Mark A. Christopherson, Shoreview, MN (US); Yelena G. Tropsha, Plymouth, MN (US); Julie M. Woessner, St. Paul, MN (US)

(73) Assignee: Medtronic, Inc., Minneapolis, MN (US)

( * ) Notice: Subject to any disclaimer, the term of this patent is extended or adjusted under 35 U.S.C. 154(b) by 2019 days.

(21) Appl. No.: 11/573,417

(22) PCT Filed: Aug. 10, 2005

(86) PCT No.: PCT/US2005/028392
§ 371 (c)(1),
(2), (4) Date: May 15, 2008

(87) PCT Pub. No.: WO2006/020696
PCT Pub. Date: Feb. 23, 2006

(65) Prior Publication Data
US 2008/0262491 A1   Oct. 23, 2008

(51) Int. Cl.
*A61B 18/14* (2006.01)
(52) U.S. Cl.
CPC ..... *A61B 18/1477* (2013.01); *A61B 2018/1475* (2013.01); *A61B 2018/1472* (2013.01)
USPC .............................................. 606/41; 606/42
(58) Field of Classification Search
USPC .......... 606/34, 42, 46, 37, 39, 40, 44; 607/98, 607/99, 115, 143
See application file for complete search history.

(56) References Cited

U.S. PATENT DOCUMENTS

| | | | | |
|---|---|---|---|---|
| 2,545,865 A | * | 3/1951 | Wallace | 606/46 |
| 4,696,684 A | * | 9/1987 | Shen | 95/266 |
| 5,334,193 A | * | 8/1994 | Nardella | 606/41 |
| 5,370,675 A | | 12/1994 | Edwards et al. | |
| 5,609,573 A | | 3/1997 | Sandock | |

(Continued)

FOREIGN PATENT DOCUMENTS

| WO | 03005918 | 1/2003 |
|---|---|---|
| WO | 03047446 | 6/2003 |

OTHER PUBLICATIONS

European Search Report issued for co-pending EP Application No. 05784963.0; Jul. 29, 2009; 6 pages.

(Continued)

*Primary Examiner* — Michael Peffley
*Assistant Examiner* — Thomas Giuliani
(74) *Attorney, Agent, or Firm* — Shumaker & Sieffert, P.A.

(57) ABSTRACT

Methods and apparatus for ablating a target tissue are discussed. Such methods and apparatus include those that simplify tissue ablation. For example, a tissue ablation device having an actuator, such as a trigger mechanism, coupled to a power source and an electrode is discussed. A single step of engaging the actuator causes the electrode to be introduced into the target tissue and causes energy to be delivered from the power supply to the tissue via the electrode. Devices that include an electrode actuator for causing the electrode to be introduced into the target tissue and a fluid actuator for causing the fluid to flow to the target tissue are also discussed. Methods of causing the electrode to be introduced into the target tissue and fluid to flow to the target tissue with a single step and more than one step are also discussed.

21 Claims, 22 Drawing Sheets

(56) References Cited

U.S. PATENT DOCUMENTS

| | | | |
|---|---|---|---|
| 5,685,877 A * | 11/1997 | Pagedas et al. | 606/46 |
| 5,762,626 A | 6/1998 | Lundquist et al. | |
| 5,964,756 A | 10/1999 | McGaffigan et al. | |
| 6,063,081 A | 5/2000 | Mulier et al. | |
| 6,238,393 B1 | 5/2001 | Mulier et al. | |
| 6,302,903 B1 | 10/2001 | Mulier et al. | |
| 6,315,777 B1 * | 11/2001 | Comben | 606/41 |
| 6,328,393 B1 | 12/2001 | Lin et al. | |
| 6,409,722 B1 | 6/2002 | Hoey et al. | |
| 6,428,538 B1 * | 8/2002 | Blewett et al. | 606/46 |
| 6,494,902 B2 | 12/2002 | Hoey et al. | |
| 6,497,705 B2 | 12/2002 | Comben | |
| 6,526,320 B2 * | 2/2003 | Mitchell | 607/101 |
| 6,537,248 B2 | 3/2003 | Mulier et al. | |
| 6,537,272 B2 | 3/2003 | Christopherson et al. | |
| 6,623,515 B2 | 9/2003 | Mulier et al. | |
| 6,706,039 B2 | 3/2004 | Mulier et al. | |
| 6,736,810 B2 | 5/2004 | Hoey et al. | |
| 6,849,073 B2 | 2/2005 | Hoey et al. | |
| 6,911,019 B2 | 6/2005 | Mulier et al. | |
| 2003/0212394 A1 * | 11/2003 | Pearson et al. | 606/41 |
| 2004/0133197 A1 * | 7/2004 | Utley et al. | 606/41 |

OTHER PUBLICATIONS

Office Action for U.S. Appl. No. 11/950,751, mailed Dec. 6, 2011, 6 pages.

Response to office action for U.S. Appl. No. 11/950,751, filed Mar. 6, 2012, 9 pages.

* cited by examiner

TUNA DEVICE WITH INTEGRATED SALINE RESERVOIR

This application is a U.S. National Stage filing of copending PCT Application Serial No. PCT/US2005/028392, filed Aug. 10, 2005, which claims the benefit of and is a continuation-in-part of U.S. patent application Ser. No. 10/915,310 entitled "TUNA DEVICE WITH INTEGRATED SALINE RESERVOIR" filed Aug. 10, 2004, now issued as U.S. Pat. No. 7,322,974, the disclosure of which is incorporated by reference herein in its entirety.

FIELD OF THE INVENTION

The disclosure relates to methods and apparatus for ablating tissue, such as Transurethral Needle Ablation (TUNA) devices, including methods and apparatus for performing tissue ablating procedures with a wet or virtual electrode.

BACKGROUND

In recent history, tissue ablation procedures have employed a "dry" electrode. Dry electrode tissue ablation systems, such as TUNA systems, typically have needle electrodes coupled to a trigger mechanism for deploying the needles. The needles are coupled to a power generator. A manual switch is typically engaged to complete a circuit allowing ablative energy to flow from the power generator to the tissue via the needles. Thus, for a typical tissue ablation device to deliver ablative energy to a tissue, an end use of the device performs at least two separate steps: 1) engaging a trigger mechanism to deploy needles and 2) engaging a switch to supply ablative energy from the power generator to the tissue via the needles. More simplified systems have not been described.

Rather, more complex systems in the form of "wet" electrode systems have been proposed. While more complex, wet electrode systems have been proposed to address some shortcomings of dry electrode systems. More particularly, the amount of power delivered and speed of lesion formation in dry electrode approaches is limited by high impedance at the electrode-tissue interface. To minimize this issue, it has been proposed to pump saline through the electrode to create a "wet" electrode. Saline increases the conductivity of the tissue to be treated, allowing for increased efficiency of tissue ablation. However, proposed wet electrode tissue ablation systems may require additional controls and equipment for delivering the saline, making wet electrode tissue ablation, such as TUNA, more complex to perform than traditional dry electrode tissue ablation.

BRIEF SUMMARY

An embodiment of the invention provides a method for ablating tissue at a target location. The method comprises introducing an electrode into the target location and applying an ablative energy to the tissue via the electrode. The electrode is introduced to the target location and the ablative energy is applied to the tissue through a single step carried out by a user of a system capable of introducing the electrode and applying the ablative energy. In various embodiments, the single step comprises engaging an actuator of the system. The system may be, for example, a TUNA system. The method may further comprise introducing a conductive fluid to the target location. The conductive fluid may be introduced in the single step, which may be engaging an actuator.

In an embodiment, the invention provides a system for ablating a target tissue at a target location. The device comprises an actuator operably coupled to an electrode and an energy source. The energy source is operably coupled to the electrode. The actuator is configured to cause the electrode to enter the target tissue and to cause the energy source to deliver ablative energy to the tissue via the electrode. The system may further comprise a fluid source. The actuator may be configured to cause fluid from the fluid source to flow to the target tissue.

An embodiment of the invention provides a method for ablating tissue at a target location. The method comprises introducing an electrode into the target location and introducing a conductive fluid to the target location. The electrode and the conductive fluid are introduced into the target location through a single step carried out by a user of a system capable of introducing the electrode and the conductive fluid. In various embodiments, the single step comprises engaging an actuator of the system. The system may be, for example, a TUNA system. The method further comprises applying energy to the target location via the electrode to ablate the tissue.

In an embodiment, the invention provides a system or device for ablating a target tissue at a target location. The system or device comprises an actuator operably coupled to a fluid source and an electrode. The actuator is configured to cause the electrode to enter the target tissue and to cause fluid from the fluid source to flow to the target tissue. The fluid source may be contained within the device, external to the device, or a combination thereof.

An embodiment of the invention provides a device for ablating a tissue at a target location. The device comprises a housing and an elongate probe member extending from the housing. The elongate probe member comprises proximal and distal ends and is provided with a passageway extending at least substantially from the proximal end to the distal end. The device further comprises an ablation needle. The ablation needle comprises proximal and distal ends and a lumen extending at least substantially from the proximal end to the distal end. The ablation needle is slidably disposed within the passageway of the elongate probe member. The device may optionally comprise a sheath. The sheath has proximal and distal ends and a lumen extending at least substantially between the proximal and distal ends. The sheath may be slidably disposed within the passageway of the elongate probe member. The needle may be slidably disposed within the lumen of the sheath. The device further comprises a reservoir capable of holding a conductive fluid. The reservoir is in fluid communication with one or more of the lumen of the sheath, the lumen of the needle, or the passageway of the elongate probe member. The device further comprises an actuator. The actuator is operably coupled to the reservoir and configured to cause the conductive fluid to flow through one or more of the lumen of the sheath, the lumen of the first needle, or the first passageway of the elongate tubular member into the target location. The actuator is also operably coupled to the proximal end of the first needle, and optionally the sheath, and configured to cause the distal end of the first needle, and optionally the sheath, to extend into the target location. In an embodiment, the device may further comprise a discharge member. The discharge member comprises proximal and distal portions. The proximal portion of the discharge member is in fluid communication with the reservoir, and the distal portion of the discharge member is in fluid communication with one or more of the lumen of the sheath, the lumen of the first needle, or the first passageway of the elongate probe member. The discharge member is coupled to the actuator such that engaging the actuator forces the conductive fluid to flow from the discharge member to the target location through one or both of the lumen of the first needle or the first passageway of the elongate probe member. The discharge member may also be coupled to the actuator such that disengaging the actuator reduces pressure in the discharge member relative to the reservoir, allowing the conductive fluid from the reservoir to be drawn into the discharge member.

An embodiment of the invention provides a device for ablating a tissue at a target location. The device comprises a housing and an elongate probe member extending from the housing. The elongate probe member has proximal and distal ends and is provided with a passageway extending at least substantially from the proximal end to the distal end. The device further comprises an ablation needle. The ablation needle comprises proximal and distal ends and a lumen extending at least substantially from the proximal end to the distal end. The needle is slidably disposed within the passageway of the elongate probe member. The device may optionally comprise a sheath. The sheath has proximal and distal ends and a lumen extending at least substantially between the proximal and distal ends. The sheath may be slidably disposed within the passageway of the elongate probe member. The needle may be slidably disposed within the lumen of the sheath. The device further comprises a tubular member comprising a lumen and adapted to permit flow of a conductive fluid. The device further comprises a valve having a proximal portion and a distal portion. The proximal portion of the valve is in fluid communication with the lumen of the tubular member, and the distal portion of the valve is in fluid communication with one or more of the lumen of the sheath, the lumen of the needle, or the passageway of the elongate probe member. The valve is configured to be moved between an open position and a closed position. The open position allows conductive fluid flow from the lumen of the tubular member to one or more of the lumen of the sheath, the lumen of the needle, or the passageway of the elongate probe member. The closed position prevents fluid flow from the lumen of the tubular member to one or more of the lumen of the sheath, the lumen of the needle, or the passageway of the elongate probe member. The device further comprises an actuator. The actuator is coupled to the valve and configured to open the valve to allow flow of conductive fluid through one or more of the lumen of the sheath, the lumen of the needle, or the passageway of the elongate tubular member into the tissue. The actuator is also coupled to the proximal end of the needle, and optionally the sheath, and adapted to cause the distal end of the needle, and optionally the sheath, to extend into the tissue.

An embodiment of the invention provides a device for ablating a target tissue, the device comprises a housing, an electrode slidably disposed within the housing, a reservoir capable of housing a conductive fluid, an electrode actuator operably coupled to the electrode, the electrode actuator being configured to cause the electrode to be introduced to the target tissue, and a fluid actuator operably coupled to the reservoir, the fluid actuator being configured to cause the fluid to flow from the reservoir to the target tissue.

An embodiment of the invention provides a method for ablating tissue at a target location comprising the steps of introducing an electrode into a target tissue location, introducing a conductive fluid into the target tissue location, and ablating the target tissue by applying energy to the target tissue via the electrode, wherein the electrode is introduced to the target location through a step and the conductive fluid is introduced to the target location through a separate step carried out by a user of a system capable of introducing the electrode and the conductive fluid.

Some embodiments of the invention may provide one or more advantages over at least one currently available or previously method, apparatus, and/or system for ablating tissue. In some embodiments, the invention may combine the efficiency and efficacy of "wet" or "virtual" electrode technology with the relative ease of conventional "dry" electrode techniques. By deploying an ablation needle and conductive fluid in a single action, the present disclosure describes at least some methods, systems and apparatuses that may simplify wet electrode tissue ablation procedures. In addition, various embodiments of the invention may simplify dry electrode techniques. For example, by configuring an actuator to be coupled to both a needle and a power source, the needle may be deployed and ablative power may be delivered in a single step. These and other advantages will become evident to one of skill in the art upon reading the disclosure herein.

The drawings are not necessarily to scale. Like numbers refer to like parts or steps throughout the drawings. However, it should be understood that use of like reference numbers are for convenience and should not be construed as limiting. For example, the use of the number "10" to refer to "device" in both FIGS. 1 and 4 does not indicate that the device of FIG. 1 must take the form of the device shown in FIG. 4.

DETAILED DESCRIPTION

In the following description, reference is made to the accompanying drawings that form a part hereof, and in which are shown by way of illustration several specific embodiments of the invention. It is to be understood that other embodiments of the invention are contemplated and may be made without departing from the scope or spirit of the present invention. The following detailed description, therefore, is not to be taken in a limiting sense.

The invention, in various embodiments, relates to methods, apparatuses, and systems employing wet electrode technology. In various embodiments, the wet electrode technology may be applied to TUNA procedures, devices and systems. Various patents and patent applications that discuss wet electrode technology and TUNA include US 20030073989 and U.S. Pat. No. 6,623,515 for example.

As those of ordinary skill in the art will readily appreciate upon reading the description herein, at least some of the devices and methods disclosed in the patents and publications cited herein may be modified advantageously in accordance with the teachings of the present invention.

Various embodiments of the invention provide methods and apparatuses for ablating tissue. The methods and apparatuses in some embodiments provide variations of currently available or previously described dry and wet electrode techniques and devices. In at least some embodiments of the invention, methods, devices and systems that are simpler to use than those described to date are provided.

Figure 1A:
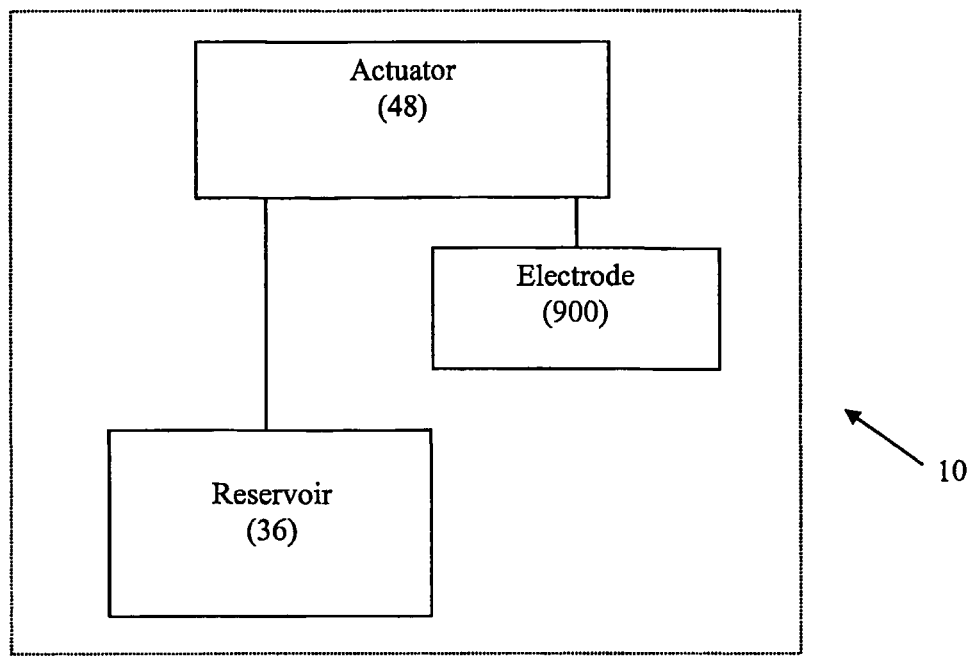
FIGS. 1A and 1B are block diagrams of systems according to embodiments of the invention.
Figure 1B:
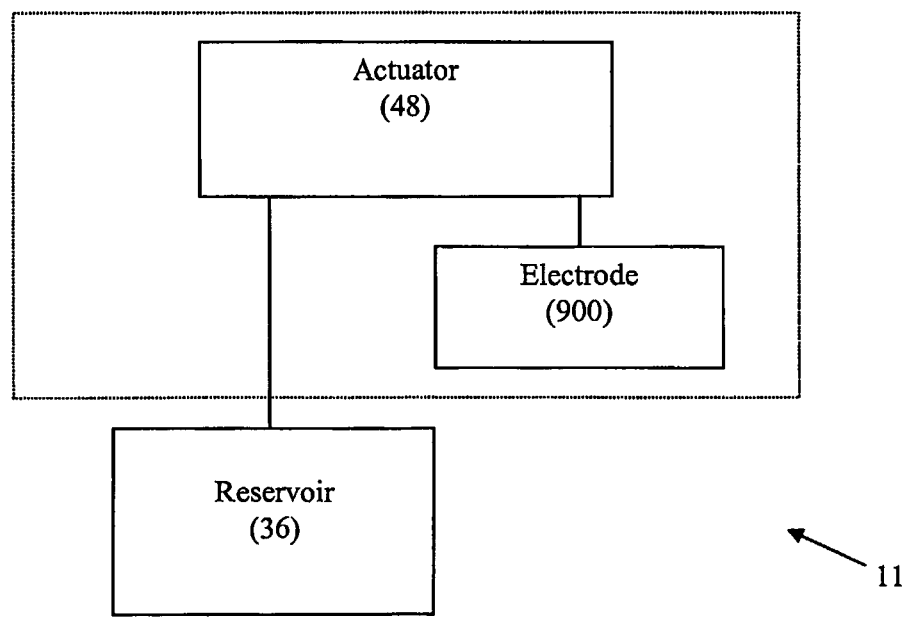

Referring to FIG. 1, an embodiment of the invention provides a tissue ablation device 10 or system 11 comprising an actuator 48 operably coupled to a fluid source reservoir 36 and an electrode 900. The actuator 48 is configured to cause the electrode 900 to enter a target tissue and to cause fluid from the reservoir 36 to flow to the target tissue. The reservoir 36 may be housed in the device 10 (FIG. 1A) or may be external to the device 10 (FIG. 1B).

Reservoir 36 may take the form of any container capable of holding a conductive fluid. Reservoir 36 is preferably made of material compatible with a conductive fluid. Non-limiting examples of materials for forming reservoir 36 include polycarbonate, polyethylene, polypropylene, polyvinyl chloride, ABS, silicone, and polyurethane. Reservoir 36, or a portion thereof, may be rigid or may be compressible. Reservoir 36 may be a part of a pump system (not shown), such as a pump system capable of delivering fluid at a constant rate. When housed within the device 10, it will be understood that the shape and size of reservoir 36 may be modified to accommodate the design of device 10.

Reservoir 36 may be capable of holding any volume of fluid, limited by the design of device 10 or system 11. Preferably reservoir 36 is capable of holding at least enough conductive fluid so that a sufficient amount of conductive fluid may be delivered to a target location during an ablation procedure. It may be desirable for reservoir 36 to be capable of holding at least about 0.1 cc to about 60 cc of fluid, as about 0.1 cc to about 5 cc of conductive fluid will be typically delivered per lesion and about 4 to about 12 lesions may be typically delivered per ablation procedure. Of course, any volume of conductive fluid may be delivered per lesion and any number of lesions may be performed per procedure.

Reservoir 36 may be permanently mounted within device 10, or may be replaceable. Replaceable reservoirs 36 may be suitable for a single tissue ablation procedure or multiple procedures. Preferably, when reservoir 36 is replaceable, reservoir 36 is configured for a single tissue ablation procedure and is prepackaged with sufficient conductive fluid for all of the lesions to be performed in the procedure.

Any electrode 900 suitable for being delivered into a target tissue location and capable of delivering an ablative lesion may be incorporated into a tissue ablation device according to various embodiments of the invention. Electrode 900 is coupled to an electrical energy source (not shown in FIG. 1), such as an RF energy source. Electrode 900 may be coupled to energy source through a conductor. Electrode 900 may be a needle of a tissue ablation device and the needle body may serve as a conductor, or portion thereof.

Embodiments of the invention provide methods for deploying an electrode, such as a needle, and delivering fluid of a tissue ablation device. One embodiment of the method comprises a single step of engaging an actuator 48. The actuator 48 being configured to cause electrode 900 to enter a target tissue location and to cause fluid from a fluid source to flow to the target tissue location. A method for ablating tissue may further comprise applying energy to the target location via the electrode 900 to ablate the tissue. Any device or system capable of deploying an electrode 900 to a target tissue location and delivering fluid to the target tissue location in a single step may be used. For example, the device or system may be a device or system as described in FIG. 1.

Figure 2A:
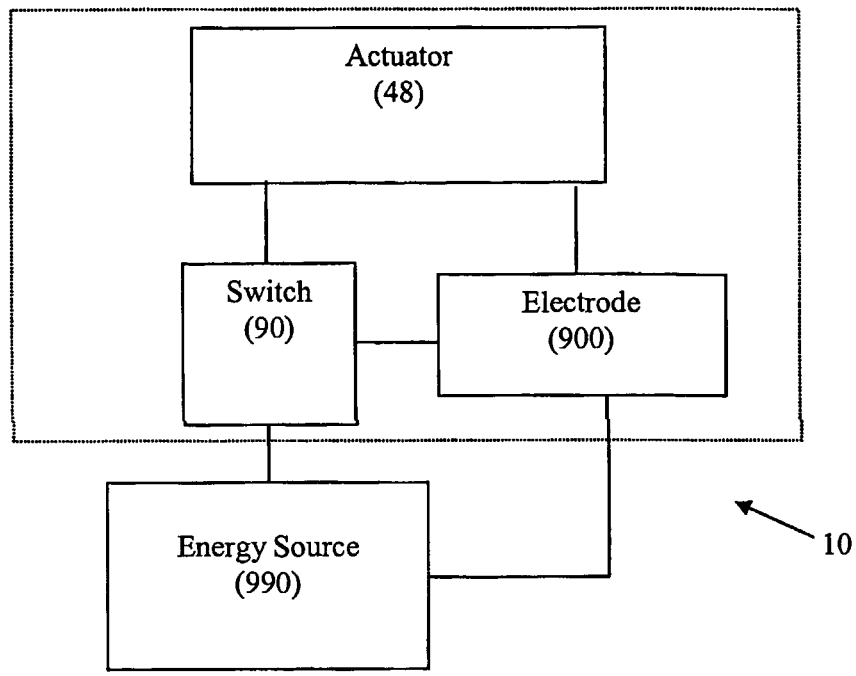
FIGS. 2A and 2B are block diagrams of a system according to an embodiment of the invention.
Figure 2B:
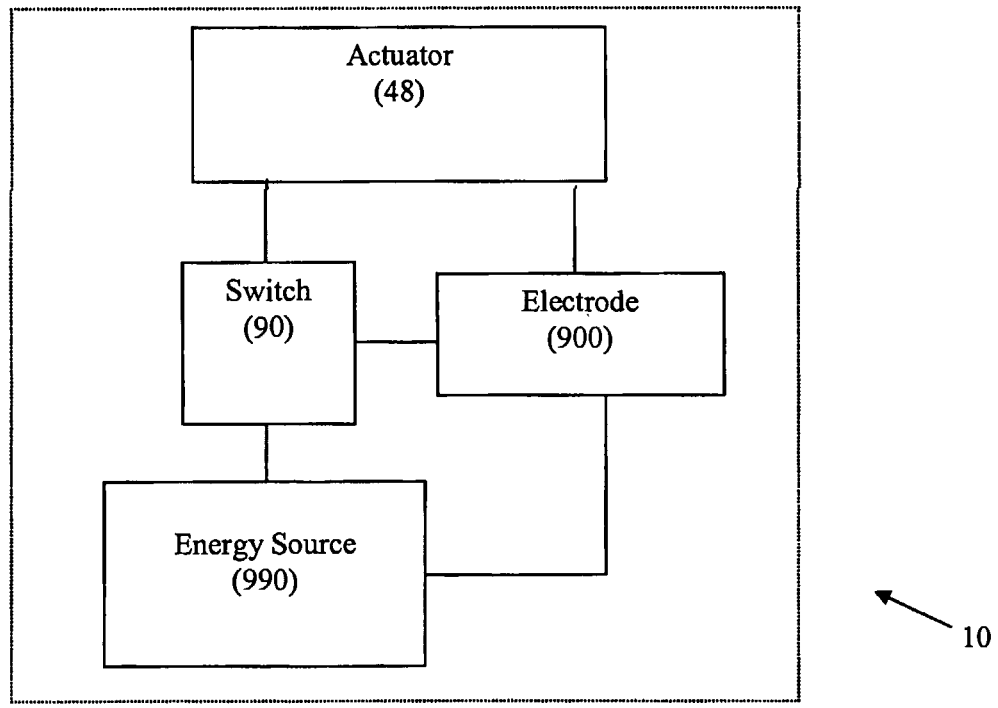

Referring to FIG. 2, an embodiment of the invention provides a tissue ablation device comprising an actuator 48 operably coupled to an electrode 900 and an energy source 990. Energy source 990, such as an RF generator, may be within device 10 or external to device 10. The actuator 48 is configured to cause the electrode 900 to enter a target tissue and to cause energy to flow from the energy source 990 to the electrode 900. Actuator 48 may be coupled to energy source 990 through a switch 90, which can allow or prevent energy flow from energy source 990 to electrode 900. For example, actuator 48 may be configured to cause switch 90 to close or complete an electrical circuit, thereby allowing energy to flow from energy source 990 to electrode 900, when actuator 48 is engaged. Also by way of example, actuator 48 may be configured to cause switch 90 to open or disconnect an electrical circuit, thereby preventing energy to flow from energy source 990 to electrode, when actuator 48 is disengaged. Alternatively, actuator 48 may be configured to prevent switch 90 from closing the circuit, as opposed to causing switch 90 to open the circuit, when actuator 48 is disengaged. The actuator may also be coupled to a fluid source reservoir 36, and be configured to and to cause fluid from the reservoir 36 to flow to the target tissue, as shown in FIGS. 3A to 3F, in a substantially similar manner as with the embodiment of FIG. 1.

Figure 3A:
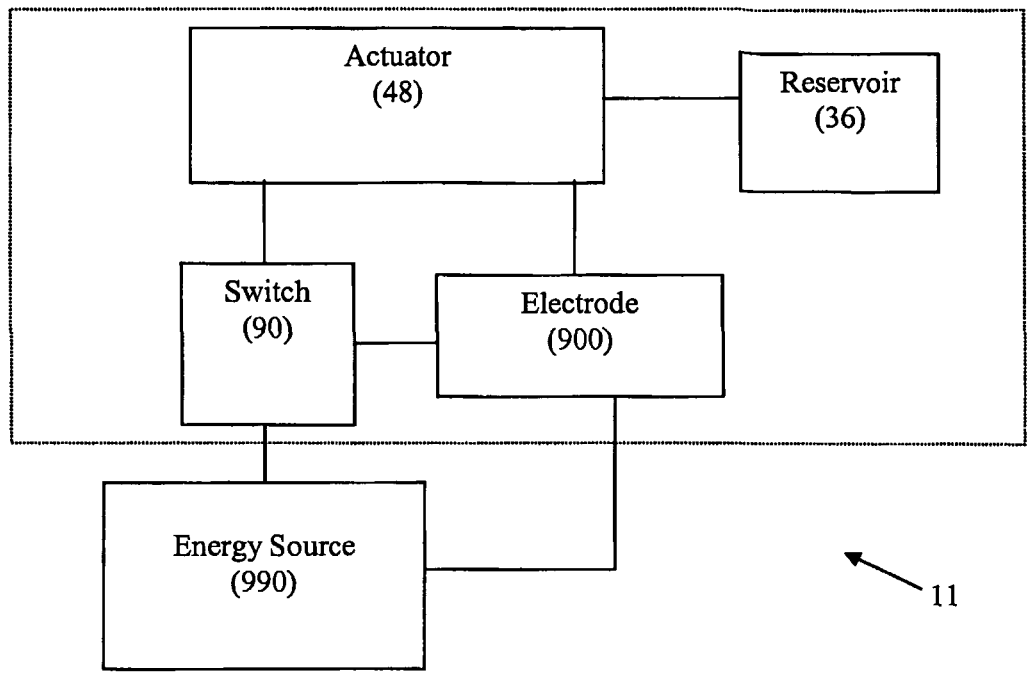
FIG. 3A to 3H are block diagrams of systems according to embodiments of the invention.
Figure 3B:
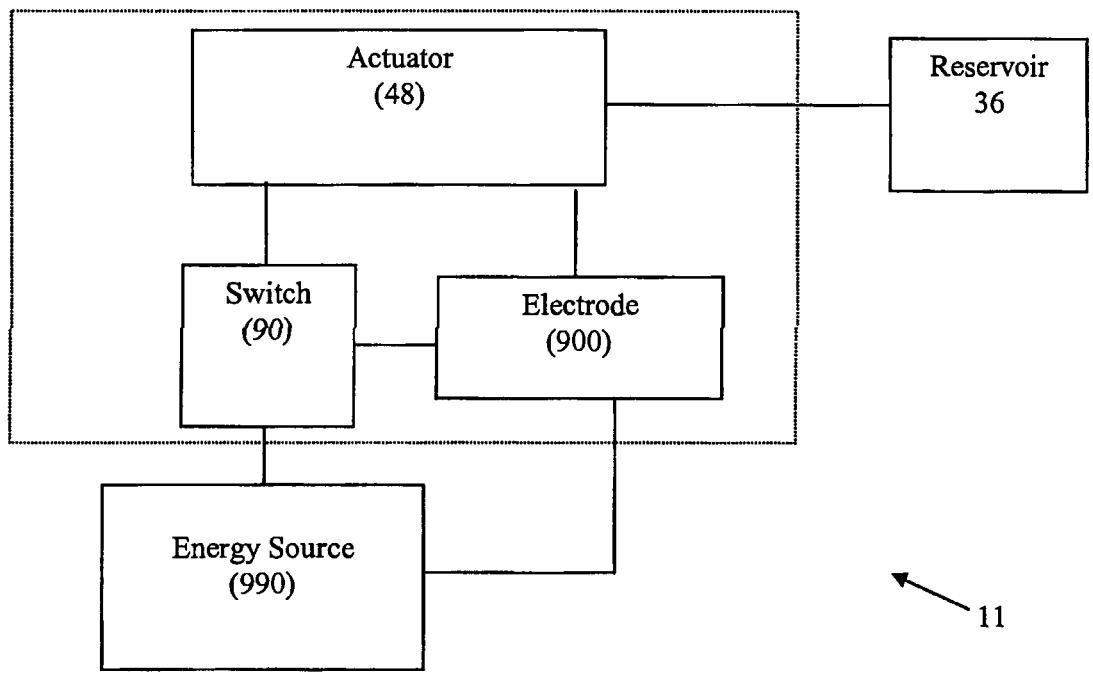
Figure 3C:
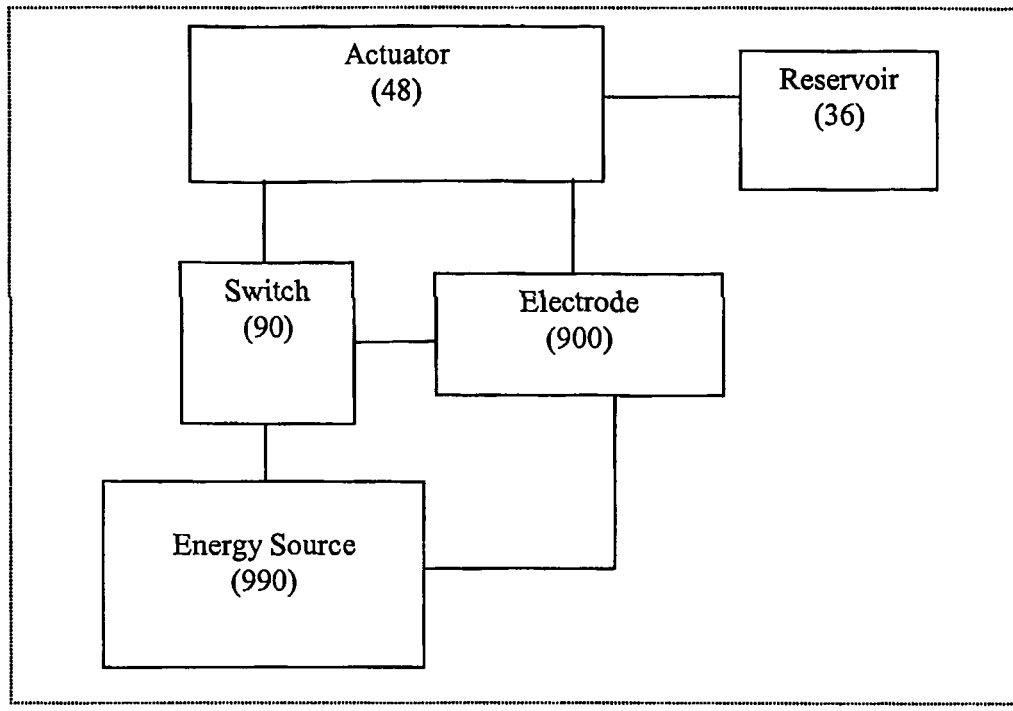
Figure 3D:
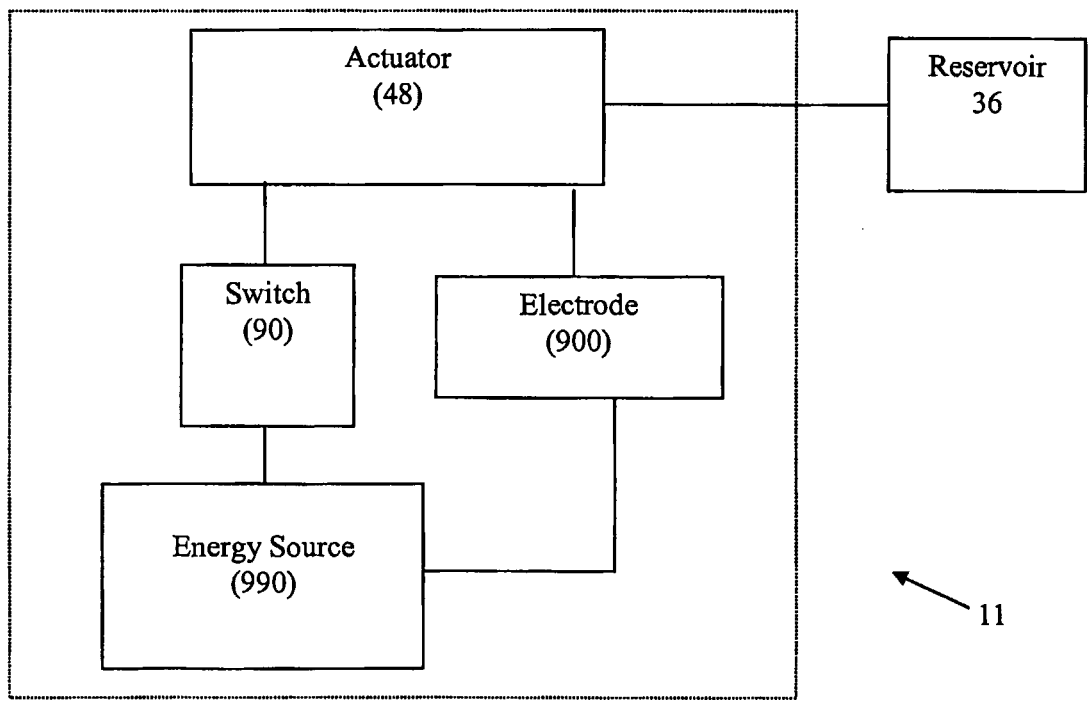
Figure 3E:
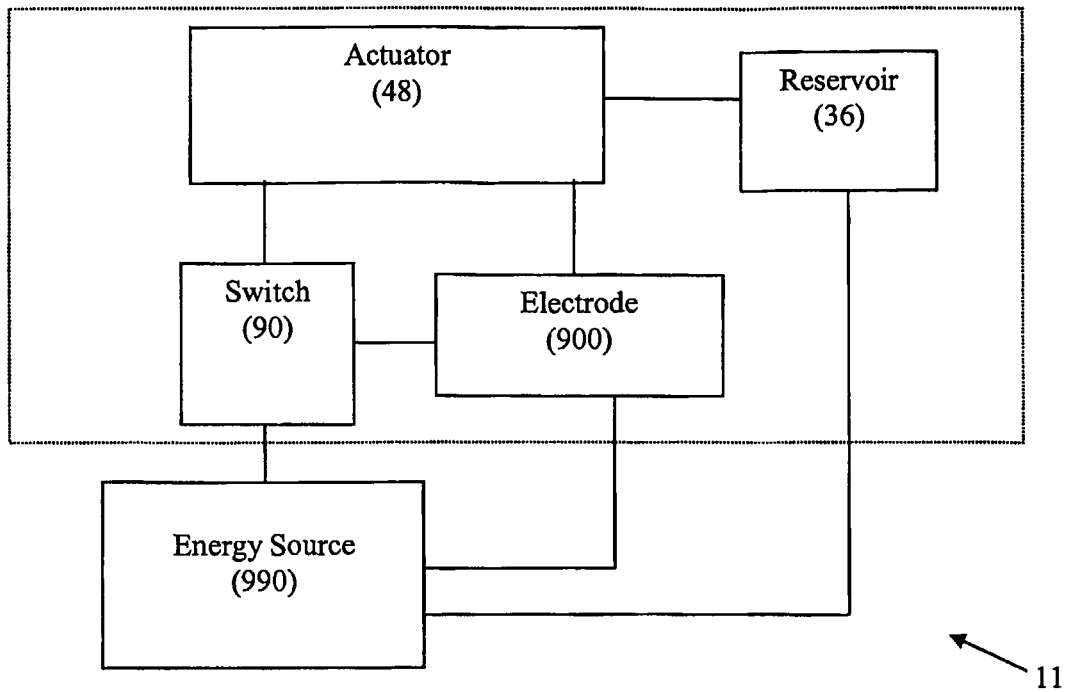
Figure 3F:
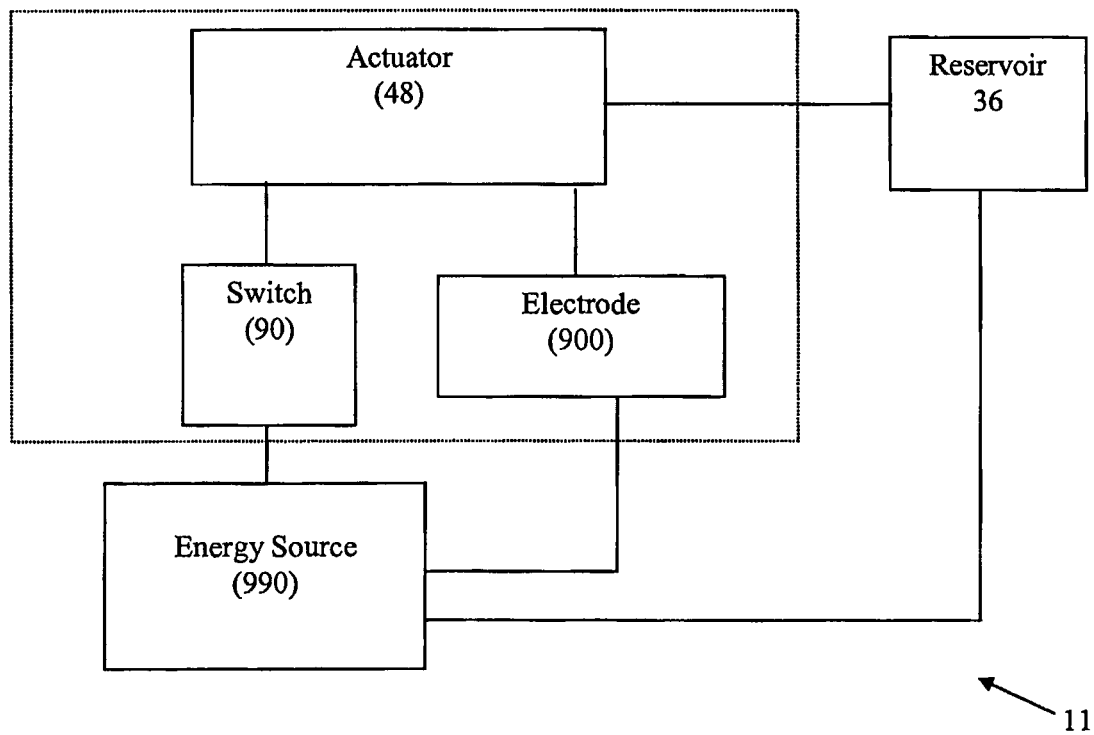
Figure 3G:
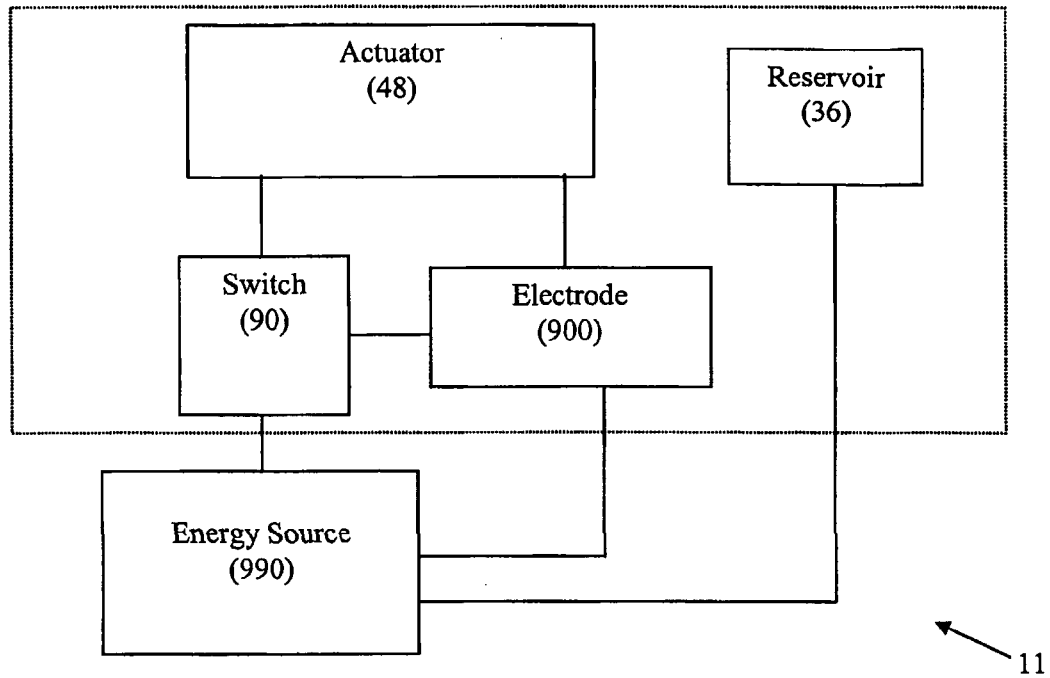
Figure 3H:
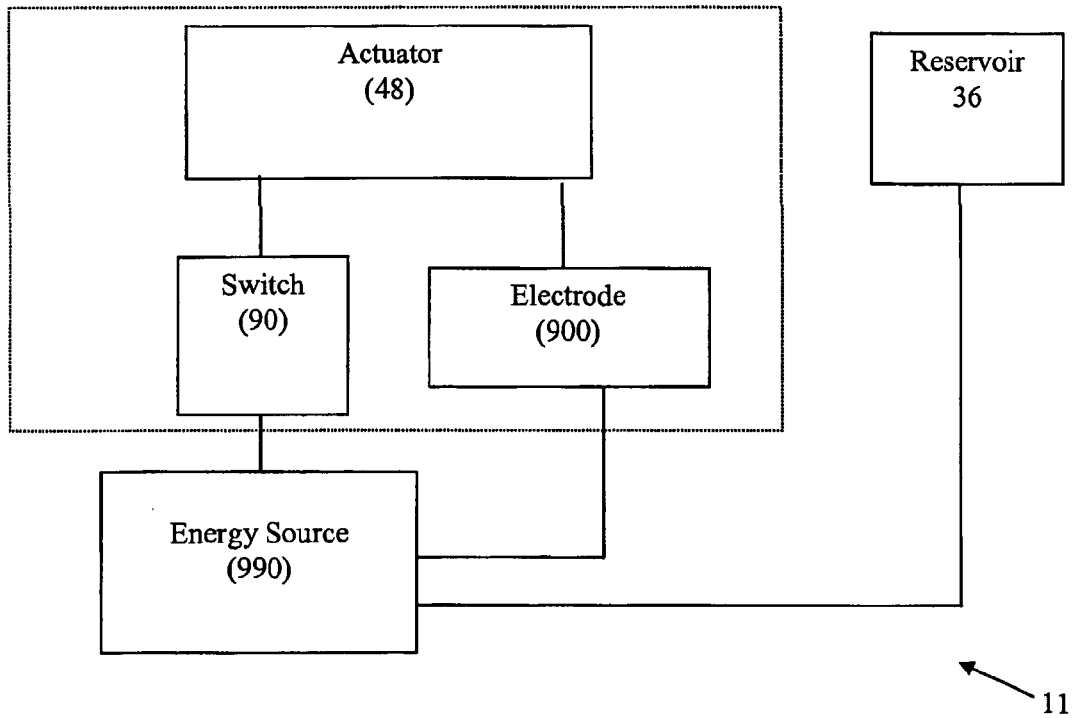

FIGS. 3E through 3H show embodiments where energy source 990 is coupled to reservoir 36. In such embodiments reservoir 36 may be coupled to energy source 990 through e.g., a pump system (not shown). The pump system may comprise the reservoir 36 and energy source 990 may provide energy to the pump system such that fluid may be pumped from reservoir 36 to the target tissue. In FIGS. 3G and 3H, actuator 48 is not coupled to reservoir 36. In such embodiments, engaging actuator 48 activates switch 90 to complete circuit, allowing energy to flow from energy source 990 to electrode 900 and to reservoir 36, which may be a part of a pump system. In FIGS. 3E and 3F, both actuator 48 and energy source 990 are coupled to reservoir 36.

Alternative coupling, whether direct or indirect, between actuator 48, energy source 990, reservoir 36, and/or electrode 900, are also contemplated. Alternative configurations are also contemplated.

Figure 13A:
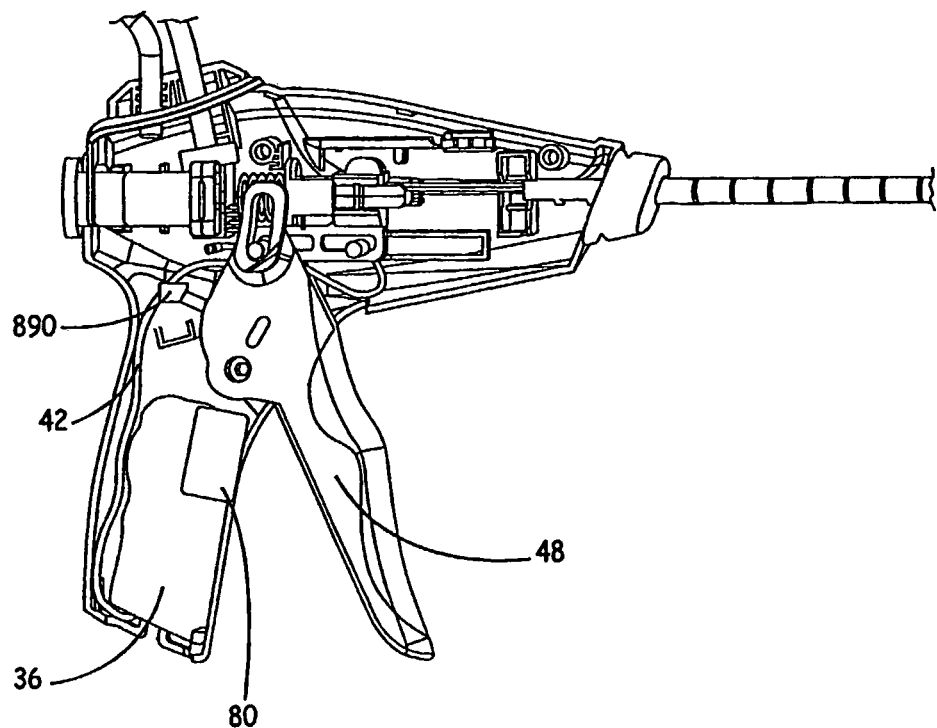
FIG. 13A to 13C is diagrammatic illustrations of a partially exposed view of a device and a schematic view of a valve according to embodiments of the invention.
Figure 13B:
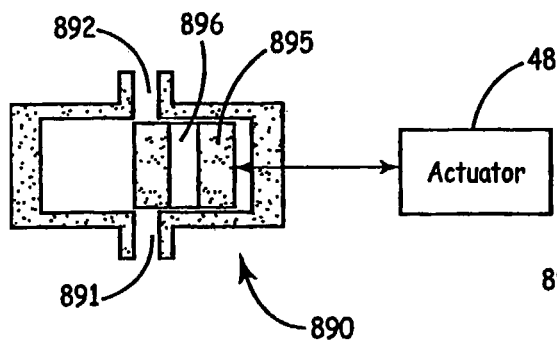

Referring to FIG. 13, an exemplary diagram showing a circuit between switch 90 and energy source 990 is shown. Switch 90 is activated to complete the circuit. Any suitable switch mechanism may be used. For example, the switch mechanism may be a momentary push button switch. The circuit may comprise a patient isolation circuit 1010 to isolate the patient electrically from unsafe voltages. The circuit may comprise a debounce circuit to filter double switch "pushes", switch "chatter", and the like. As shown in FIG. 13B, the circuit may comprise a controller of fluid flow 1030. The controller 1030 may be hardware or software. The controller 1030 may be integrated into the circuit by a switch, such as e.g. push on switch, a push off switch, push and hold on switch, release off switch, and the like.

As used herein, "single step" means a single action and may be an action comprising separate parts. For example, the single step may be engaging an actuator 48. The separate parts may be (a) partially engaging the actuator 48 to a first position and then completely engaging the actuator 48 from the partially engaged state, (b) partially engaging the actuator 48 to a first position, further engaging the actuator 48 the a second position, and further engaging the actuator 48 to a third position, and (c) the like. In an embodiment, when the engaged to a first position or during engagement to the first position the actuator 48 may be configured to cause one or more of (i) an electrode to be introduced to a target tissue, (ii) fluid to flow from a reservoir to the target tissue, or (iii) energy from an energy supply to be delivered to the target tissue via the electrode. In an embodiment, when engaged to a second position or during engagement to the second position the actuator 48 may be configured to cause one or more of (i) an electrode to be introduced to a target tissue, (ii) fluid to flow from a reservoir to the target tissue, or (iii) energy from an energy supply to be delivered to the target tissue via the electrode. In an embodiment, when the engaged to a third position or during engagement to the third position the actuator 48 may be configured to cause one or more of (i) an electrode to be introduced to a target tissue, (ii) fluid to flow from a reservoir to the target tissue, or (iii) energy from an energy supply to be delivered to the target tissue via the electrode.

Figure 4A:
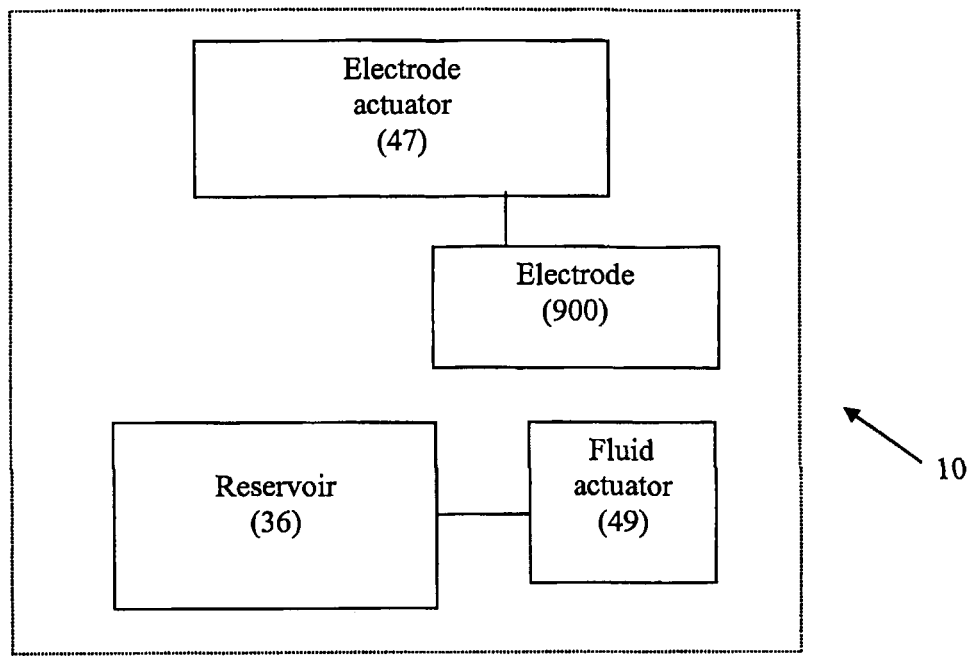
FIGS. 4A and 4B are block diagrams of systems according to embodiments of the invention.
Figure 4B:
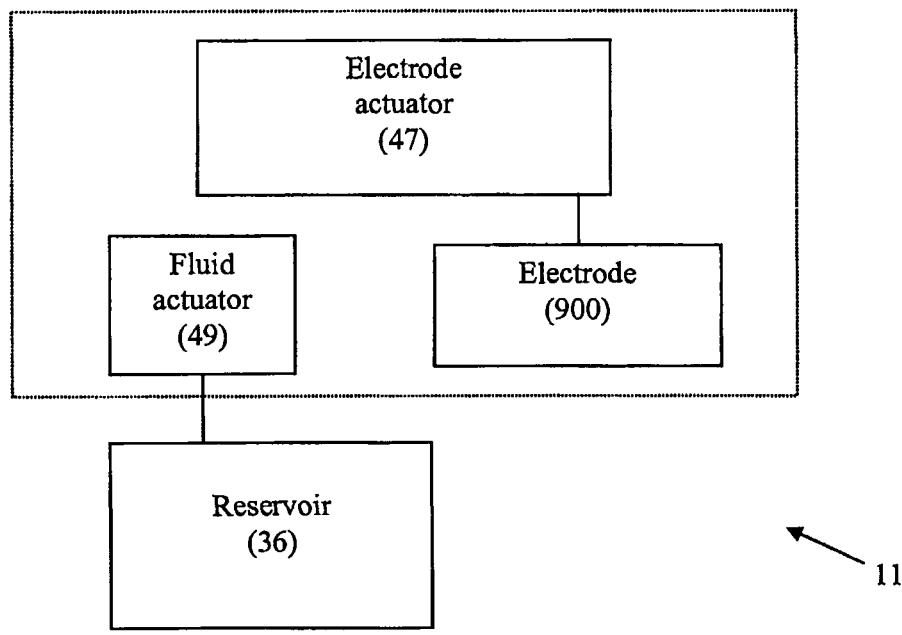

Referring to FIGS. 4A and 4B, two embodiments of the invention include a tissue ablation device 10 or system 11 comprising an electrode actuator 47 operably coupled to an electrode 900 and a fluid actuator 49 operably coupled to a reservoir 36. The electrode actuator 47 is configured to cause the electrode 900 to enter a target tissue location and the fluid actuator 49 is configured to cause fluid from the reservoir 36 to flow to the target tissue. The reservoir 36 may be housed in the device 10 (FIG. 4A) or may be external to the device 10 (FIG. 4B). The reservoir 36, and electrode 900 can be similar to those discussed above with respect to FIGS. 1A and 1B for example, and will not be discussed further.

Another embodiment of the invention provides methods for deploying an electrode, such as a needle, and delivering fluid of a tissue ablation device that includes a step of causing an electrode 900 to enter a target tissue location and a separate step of causing fluid from a fluid source such as a reservoir 36 to flow to the target tissue location. In such an embodiment, an electrode actuator 47 can be configured to cause electrode 900 to enter a target tissue location and a fluid actuator 49 can be configured to cause fluid from a fluid source to flow to the target tissue location. A method for ablating tissue may further include applying energy to the tissue location via the electrode 900 to ablate the tissue.

One embodiment of such a method can include only one step where the fluid actuator 49 causes fluid from a fluid source to flow to the target tissue location, in such an embodiment, the fluid flow can be maintained during the entire procedure. In another embodiment, a method includes more than one step where the fluid actuator 49 causes fluid flow from a fluid source to flow to the target tissue location. In one example of this embodiment, the fluid flow is ceased at least once, and then it is caused to flow to the target location again. In an embodiment such as this, where the fluid flow is not continuous, subsequent steps of activating the fluid actuator 49 can be in response to, for example, an increase in the temperature of the target tissue location, a decrease in the conductivity of the target tissue location, a desire to deliver a compound that is contained within the conductive fluid, some combination thereof, or similar considerations which would be known to one of skill in the art having read this specification.

In an embodiment where the electrode actuator 47 and the fluid actuator 49 are activated in separate steps, the fluid actuator 49 can be activated at the same time as the electrode actuator 47. In another embodiment where the electrode actuator 47 and the fluid actuator 49 are activated in separate steps, the fluid actuator 49 can be activated before the electrode actuator 47 is activated. In yet another embodiment where the electrode actuator 47 and the fluid actuator 49 are activated in separate steps, the fluid actuator 49 can be activated after the electrode actuator 47 is activated. In embodiments where the fluid actuator 49 is activated more than once, it can also be activated the first time either simultaneous with, before, or after the electrode actuator 47 is activated.

FIGS. 5A to 5F depict exemplary embodiments of a device of the invention that include an electrode actuator 47 that is operably coupled to an energy source 990 and an electrode 900. In such an embodiment, the electrode actuator 47 may be coupled to energy source 990 through a switch 90, which can allow or prevent energy flow from energy source 990 to electrode 900. Energy source 990, such as an RF generator, may be within device 10 or external to device 10. The electrode actuator 47 is configured to cause the electrode 900 to enter a target tissue and to cause energy to flow from the energy source 990 to the electrode 900. Electrode actuator 47 may be coupled to energy source 990 through a switch 90, which can allow or prevent energy flow from energy source 990 to electrode 900. For example, electrode actuator 47 may be configured to cause switch 90 to close or complete an electrical circuit, thereby allowing energy to flow from energy source 990 to electrode 900, when electrode actuator 47 is engaged. Also by way of example, electrode actuator 47 may be configured to cause switch 90 to open or disconnect an electrical circuit, thereby preventing energy to flow from energy source 990 to electrode, when electrode actuator 47 is disengaged. Alternatively, electrode actuator 47 may be configured to prevent switch 90 from closing the circuit, as opposed to causing switch 90 to open the circuit, when electrode actuator 47 is disengaged. One example of an embodiment of a device of the invention that could be utilized to deliver more fluid to the target tissue based on changes in the conductivity of the target tissue could also include a component to measure the conductivity of the target tissue. Such a device could measure the conductivity at least once and then a physician, or a program associated with the device could determine if more fluid should be delivered from the reservoir 36.

Figure 5A:
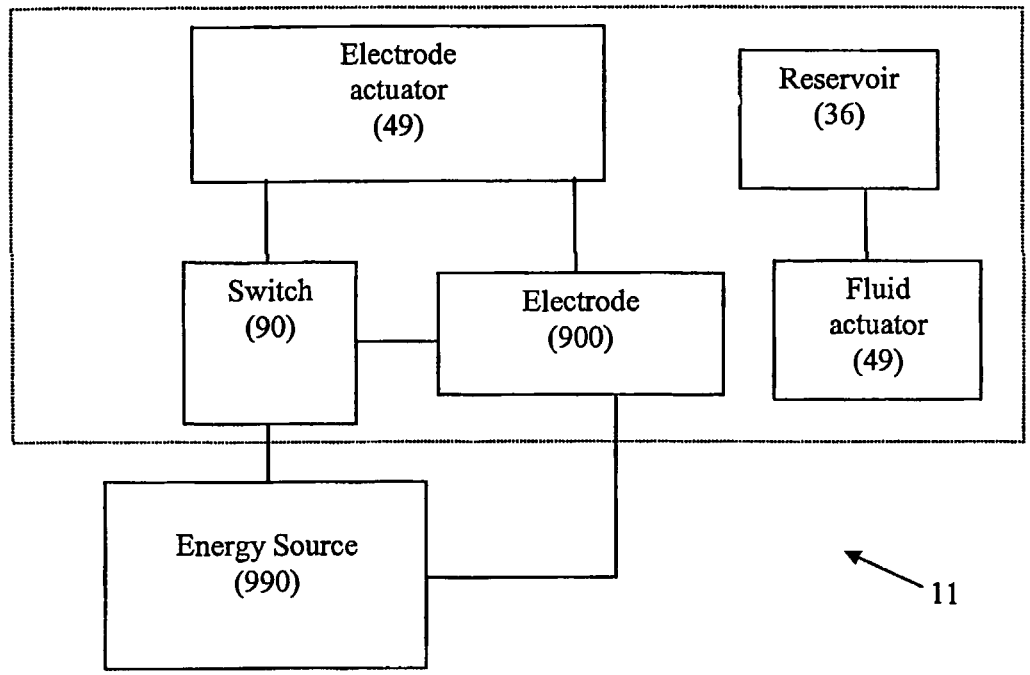
FIGS. 5A and 5F are block diagrams of systems according to embodiments of the invention.
Figure 5B:
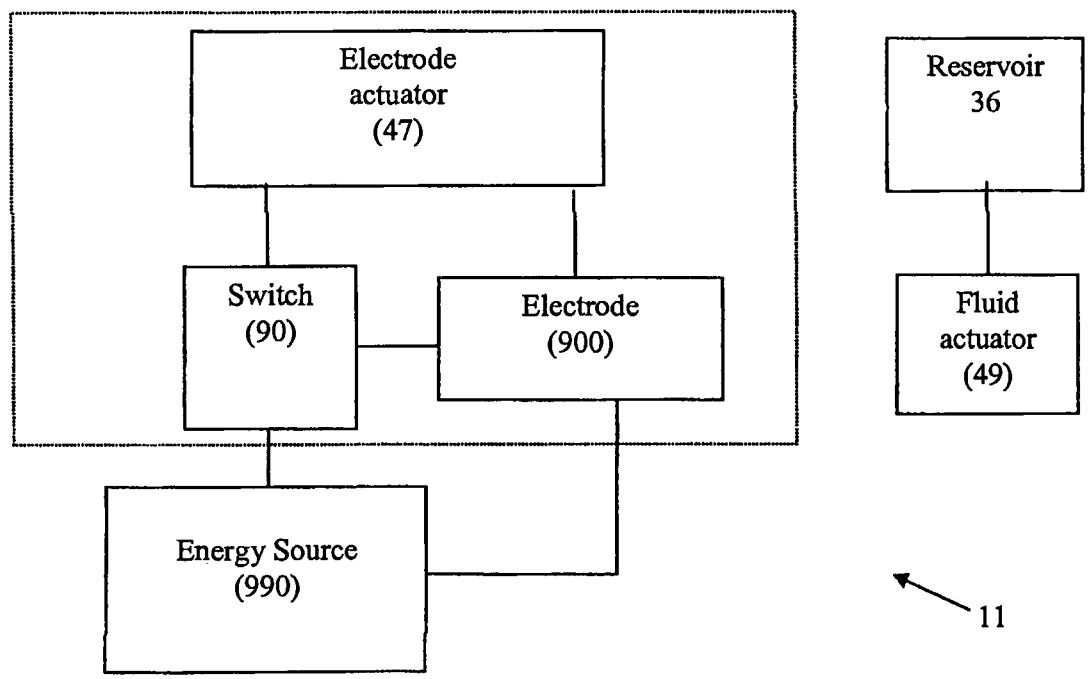
Figure 5C:
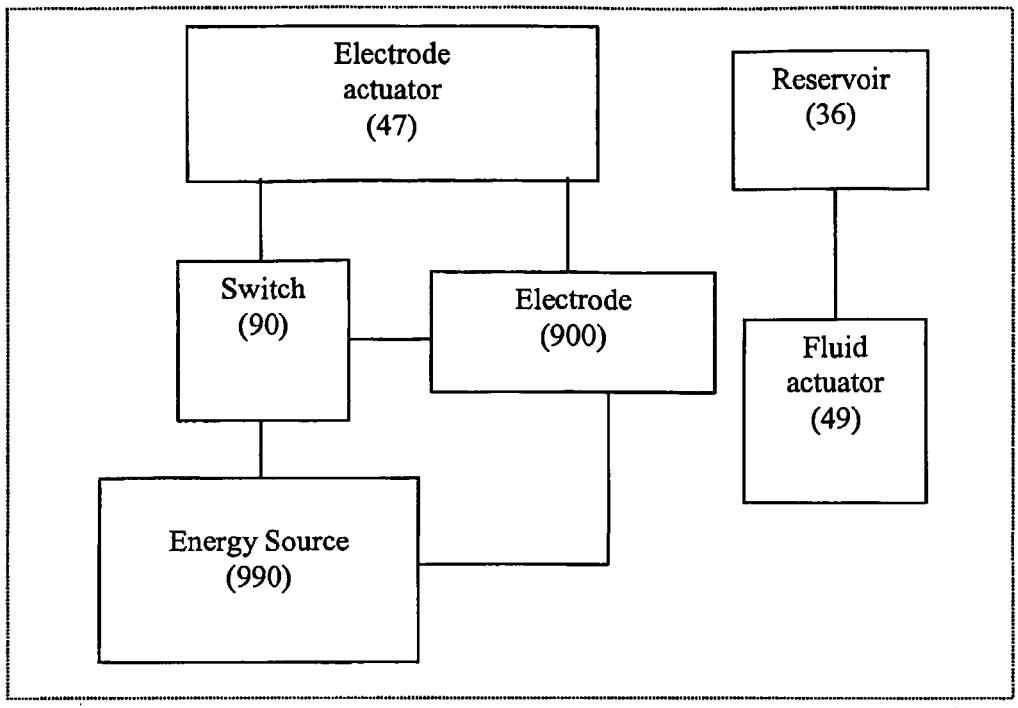
Figure 5D:
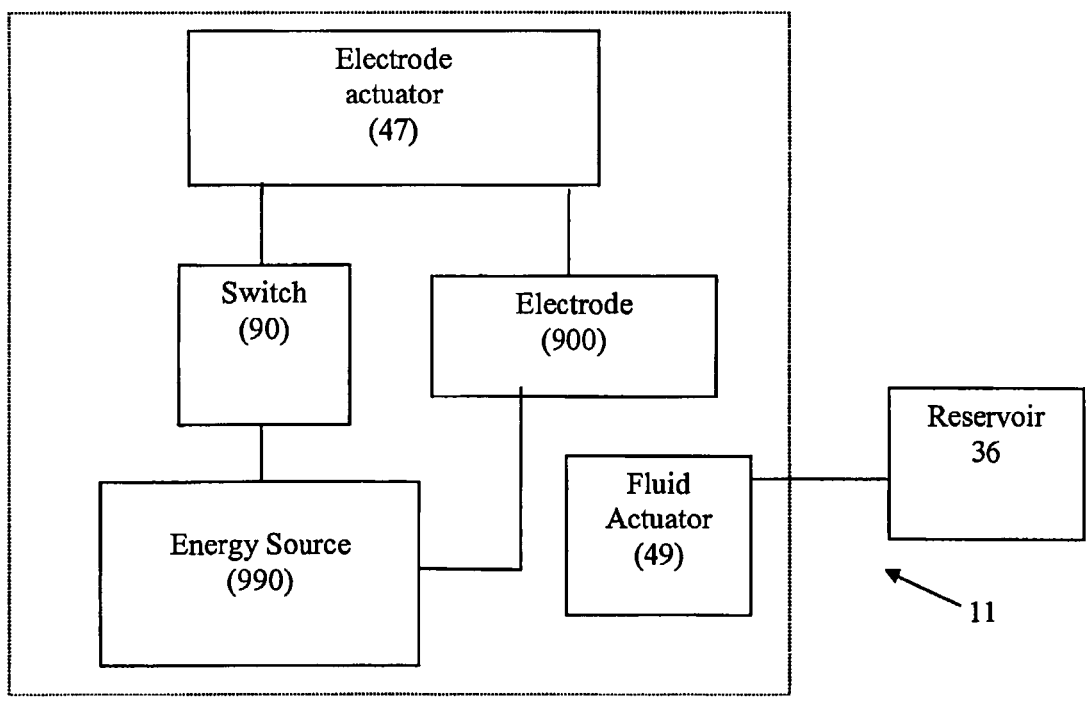
Figure 5E:
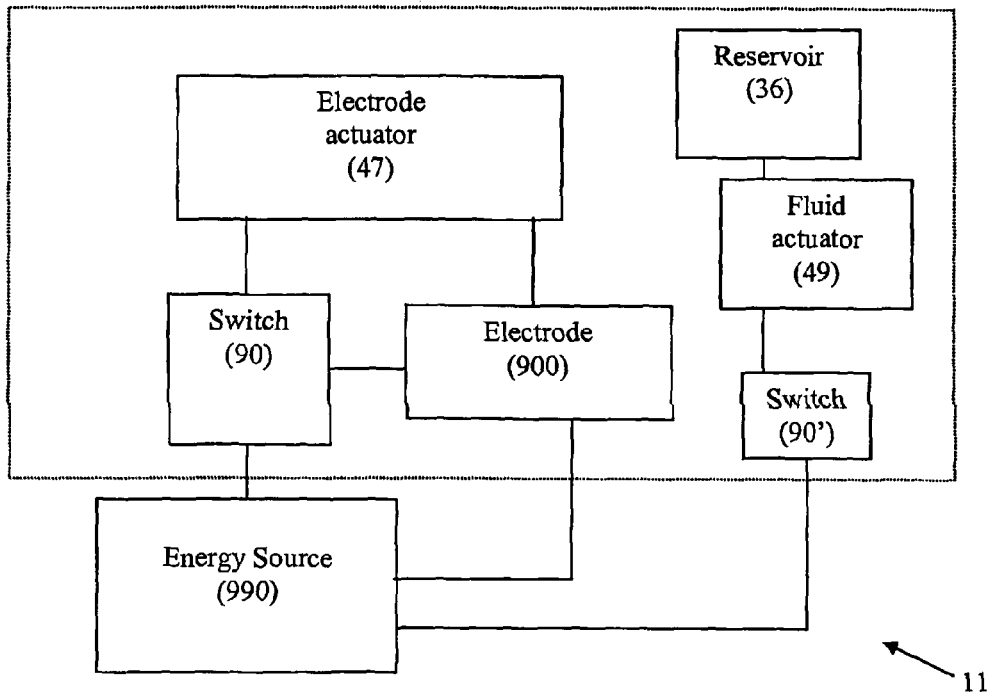
Figure 5F:
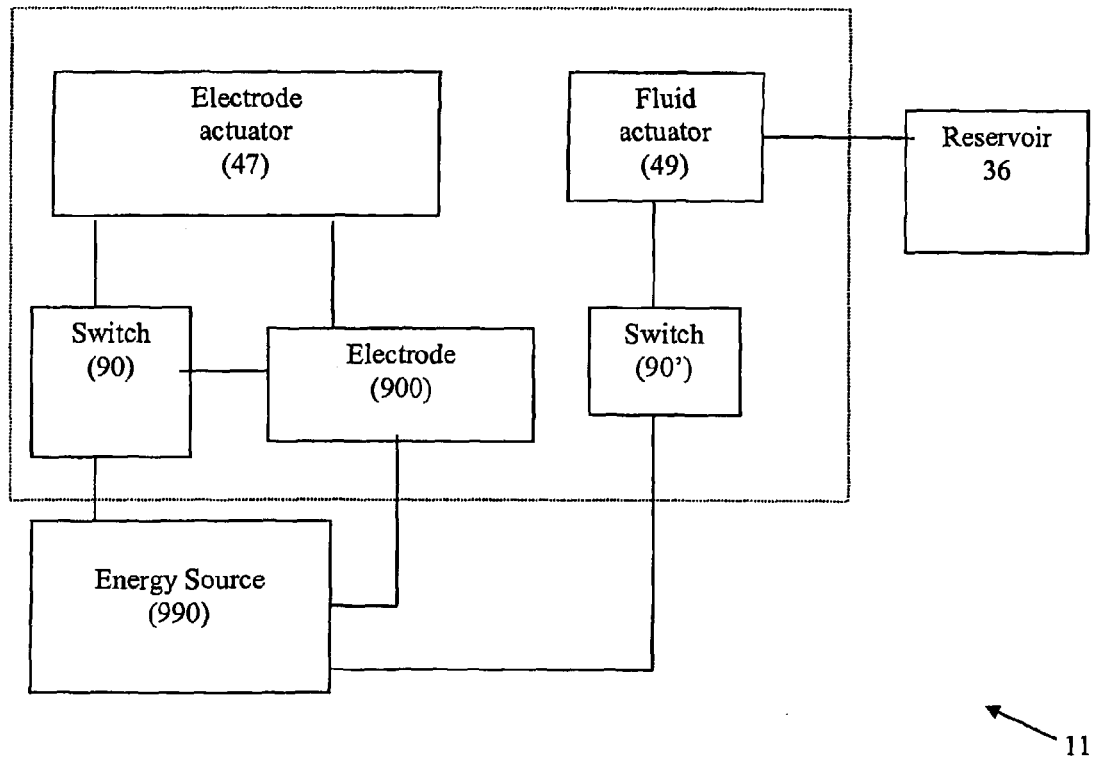

The fluid actuator 49 is also depicted in these figures coupled to a fluid reservoir 36. FIGS. 5E and 5F depict embodiments where energy source 990 is coupled to reservoir 36. In such an embodiment the reservoir 36 may be coupled to energy source 990 through for example, a pump system (not shown). The pump system may include the reservoir 36 and other components (not shown), and energy source 990 may provide energy to the pump system such that fluid may be pumped from reservoir 36 to the target tissue location. In FIGS. 5E and 5F, fluid actuator 49 activates switch 90' to complete the circuit, allowing energy to flow from energy source 990 to reservoir 36 (which may be part of a pump system) which causes fluid to flow to the target tissue location.

The methods and apparatuses of various embodiments of the invention may be used to treat a disease or disorder in a mammal, such as a human patient. Such apparatuses may be part of a system 11 and may be in the form of a transurethral needle ablation apparatus or device 10 similar to the apparatus shown in U.S. Pat. No. 5,964,756 and in U.S. Pat. No. 6,638,275, the entire content of each of which is incorporated herein by reference. An exemplary device 10 and system 11 that may be modified according to the teachings of the present invention is Medtronic's PRECISION™ Plus TUNA System. The PRECISION™ Plus TUNA System, devices, and components thereof, as well as associated Medtronic brochures and user guides could be utilized in devices of the invention, as would be known to one of skill in the art, having read this specification.

Figure 6:
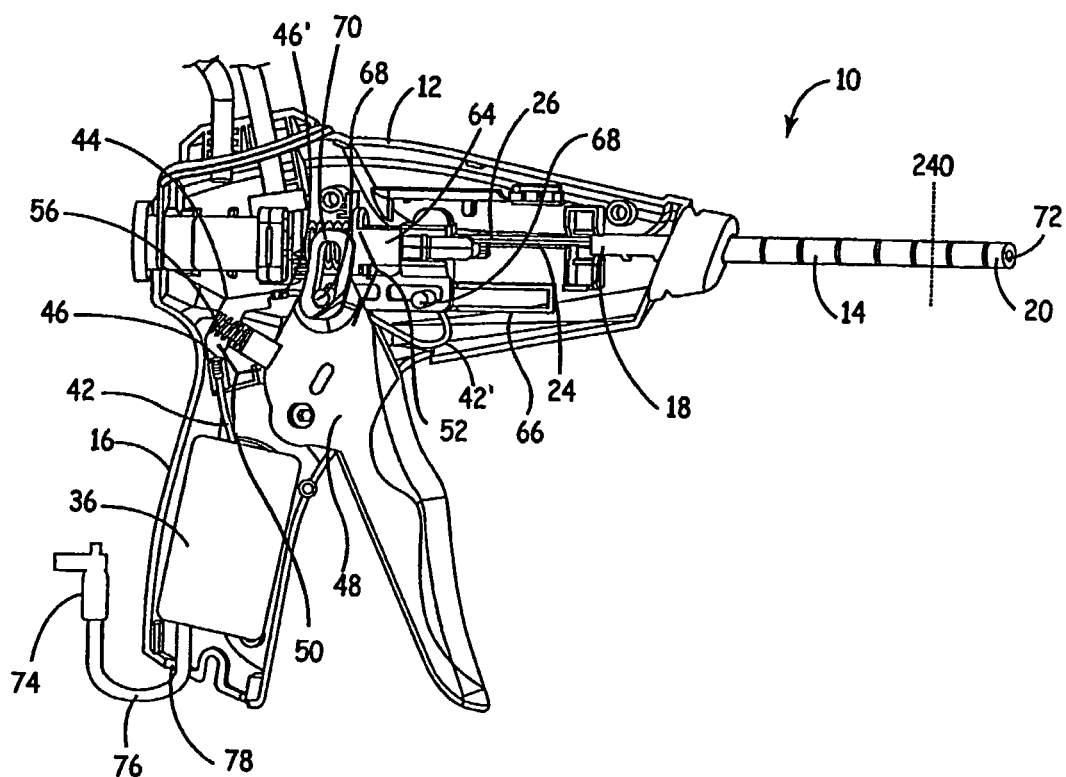
FIG. 6 is a diagrammatic illustration of a view of a partially exposed view of a device according to an embodiment of the invention.

An embodiment of the invention provides a device 10 for ablating tissue. As shown in FIG. 6, the device 10 comprises a housing 12 and an elongate probe member 14 extending from the housing 12. The housing may comprise a handle 16 extending from the housing 12. The elongate probe member comprises a proximal end 18 and a distal end 20, and one or more passageways 22 (see, e.g. FIG. 9) extending at least substantially between the proximal end 18 of the elongate probe member 14 to the distal end 20 of the elongate probe member 14. The device 10 further comprises one or more needles 24.

Figure 9:
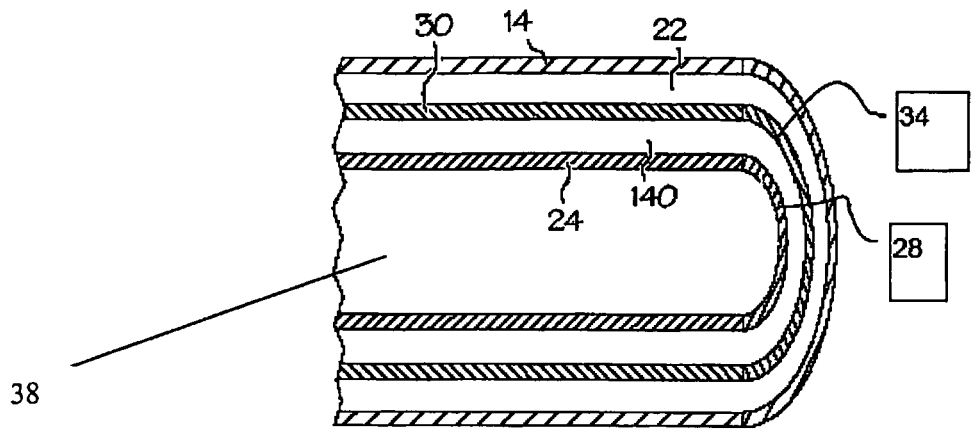
FIG. 9 is a diagrammatic illustration of a longitudinal section of a portion of a device as in FIG. 6.

As shown in FIG. 9, the one or more needles 24 may be slidably mounted within one of the one or more passageways 22 of the elongate probe member 14. The needle 24 may comprise a lumen 38 extending at least substantially between a needle proximal end 26 and a needle distal end 28. The device 10 may further comprise one or more sheaths 30 (not shown in FIG. 6). A sheath 30 has a proximal end and a distal end 34, and a lumen 40 extending at least substantially between the sheath proximal end and the sheath distal end 34. The sheath(s) 30 is slidably mounted within the one or more passageways 22 of the elongate probe member 14. When the device 10 comprises a sheath 28, a needle 24 may be slidably disposed within the lumen 40 of sheath 28. The sheath may be an insulative sheath 28.

Referring to FIG. 6, the device 10 further comprises a reservoir 36. The reservoir 36 is operably coupled to, and in fluid communication with, one or more lumens 38 of one or more needles 24, one or more lumens 40 of one or more sheaths 30, and/or one or more passageways 22 of elongate probe member 14. The reservoir 36 may be coupled to the passageway(s) 22 or lumens 38/40 via tubing 42. Any suitable tubing material, such as PVC, silicone, or polyurethane, may form tubing 42. As shown in FIG. 6, tubing 42 may be inserted into reservoir 36 and extend to discharge member 44. Discharge member 44 may be formed of any suitable material. By way of example, discharge member 44 may be formed of polycarbonate, polyethylene, polypropylene, or ABS. A one-way valve 46 may be coupled to tubing 42 to allow flow of conductive fluid from the reservoir 36 to the discharge member 44 and to prevent flow of fluid from the discharge member 44 to the reservoir 36. One-way valve 46 may be made be, e.g., a silicone valve, a Teflon valve, or a polyurethane valve. The one-way valve 46 in FIG. 6 is shown in proximity to discharge member 44, but it will be understood that one-way valve 46 may be coupled to tubing 42 at any location between reservoir 36 and discharge member 44. Tubing 42' may be used to couple discharge member 44 to needle lumen(s) 38, sheath lumen(s) 40 and/or passageway(s) 22 (only connection to needle 24 shown in FIG. 8).

A fill valve 74 may be connected to the reservoir 36 to fill or refill reservoir 36 with fluid. As shown in FIG. 6, fill valve 74 may be connected to reservoir through fill tubing 76. A supply of fluid (not shown) may be connected to fill valve 74. The supply of fluid may be under constant pressure, such that opening the valve, allows fluid to flow into reservoir 36. Fill valve 74 may comprise a stopcock or other suitable means, and the stopcock or other suitable means may be turned or engaged to allow fluid to flow into reservoir 36. Fill tubing 76 may extend from handle 16, through an opening 78 in handle 16 to allow external access to fill valve 74. Of course fill valve 76 may be placed anywhere with respect to housing 12. For example, fill valve 76 may be attached to handle 16. Fill valve 74 may also be directly coupled to reservoir 36, such that fill tubing 76 is omitted from device 10. Of course, any suitable means for filling or refilling reservoir 36 and for reservoir 36 access may be used. For example, an access port (not shown) may be used. Access port may comprise a septum, through which a needle may be inserted. Access port may be directly coupled to reservoir 36 or may be coupled to fill tubing 76, which is coupled to reservoir 36.

An O-ring or other suitable seal may be used to create a fluid-tight seal between tubing 22 and reservoir 36, tubing 22, 22' and discharge member 44, fill tubing 76 and reservoir 36, etc.

Figure 8:
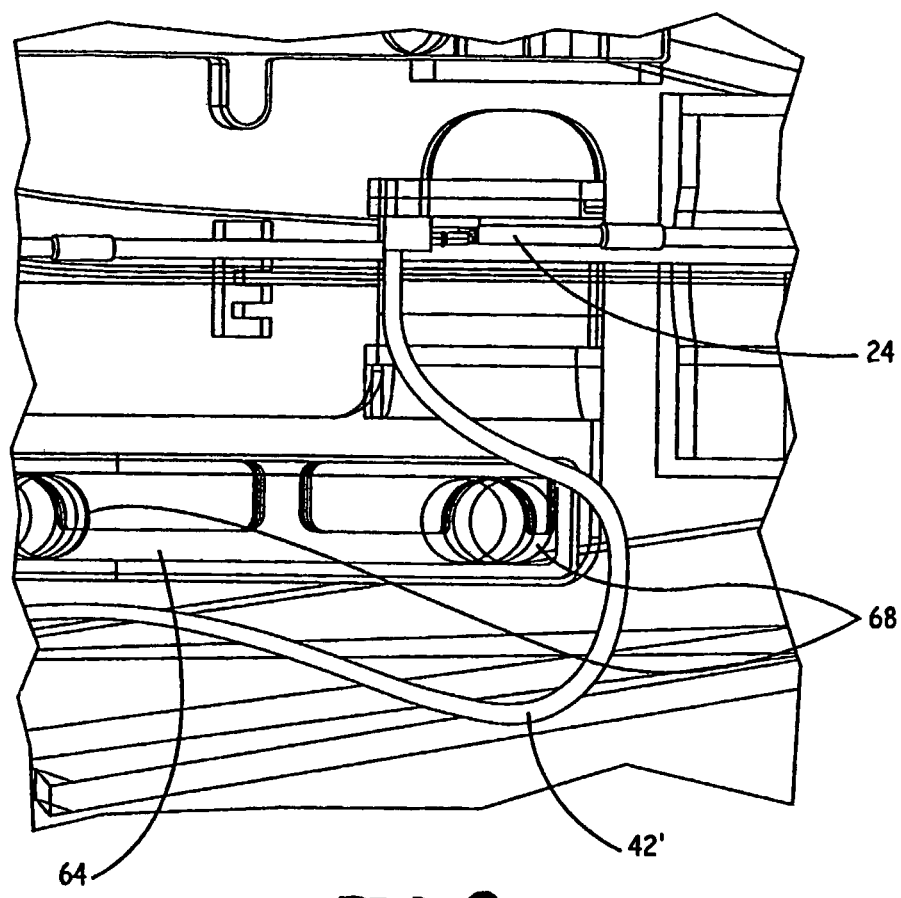
FIG. 8 is a diagrammatic illustration of an exploded view of a portion of a partially exposed device as in FIG. 6.

As shown in FIG. 8, tubing 42' is coupled to needle 24 such that a lumen of the tubing is in fluid communication with a lumen 38 of needle 24. While not shown, it will be understood that similar connections may be made such that a lumen of tubing 42' may be in fluid communication with a sheath lumen 40 and/or passageway 22. It will be further understood that tubing 42' may comprise multiple lumens through which the tubing may be placed in fluid communication with one or more needle lumens 38, one or more sheath lumens 40, and/or one or more passageways 22. The multiple lumens may be concentric, side-by-side, etc. A Y-connector (not shown) may be used to couple tubing 42' to more than one, e.g., needle 24. Alternatively, a plurality of tubing 42' may be run from discharge member 44 to a plurality of needles 24. A one-way valve 46' may be coupled to tubing 42' to allow fluid to flow from discharge member 44 to needle lumen 38, sheath lumen 40, and/or passageway 22, and to prevent flow from needle lumen 38, sheath lumen 40, and/or passageway 22 to discharge member 44. The one-way valve 46' in FIG. 8 is shown in proximity to discharge member 44, but it will be understood that one-way valve 46' may be coupled to tubing 42' at any location between discharge member 44 and needle lumen 38, sheath lumen 40, and/or passageway 22.

The device further comprises an actuator 48 extending from the housing 16. The actuator 48 comprises a fluid delivery portion 50 and a needle delivery portion 52. The fluid delivery portion 44 is operably coupled to the reservoir 36 and adapted to cause fluid to flow from the reservoir to needle lumen 38, sheath lumen 40, and/or passageway 22 and into body tissue. As shown in FIG. 6, the fluid delivery portion 50 of actuator 48 is coupled to discharge member 44. A fluid tight seal is formed between discharge member 44 and fluid delivery portion 50 of actuator. A biasing element 56, in the form of a spring coil in FIG. 6, is disposed within discharge member 44. A first end portion of biasing element 56 is configured to engage an internal surface of discharge member 44. A second end portion of biasing element 56 is configured to engage fluid delivery portion 50 of actuator 48. Biasing element 56 facilitates return of actuator 48 to a disengaged position after the actuator 48 is engaged. Of course, biasing element 56 may be placed in any location within device 10 to accomplish the return of the actuator 48 to a disengaged position. Alternatively, biasing element 56 may not be present in device 10.

Fluid delivery portion 50 of actuator 48, in combination with reservoir 36 and discharge member 44, may utilize squirt gun type technology to draw fluid from reservoir 36 and deliver the fluid to needle lumen 38, sheath lumen 40, and/or passageway 22. It will be understood that the device 10 may be primed, by for example engaging and disengaging the actuator 48, prior to using the device. Priming allows fluid to be loaded in fluid path between reservoir 36 and one or more needle lumens 38, one or more sheath lumen 40, and/or one or more passageway 22 of elongate probe member 14, such that a subsequent engagement of actuator 48 will cause the fluid to flow into a target tissue area. In the embodiment depicted in FIG. 6, a portion of fluid delivery portion 50 of actuator 48 is disposed within biasing element 56 coil. Engaging the actuator 48 inserts at least a portion of fluid delivery portion 50 into discharge member 44, increasing pressure in the discharge member 44 relative to lumen of tubing 42' and forcing fluid from discharge member to lumen of tubing 42' and one or more needle lumens 38, one or more sheath lumens 40, and/or one or more passageways 22 of elongate probe member 14. Disengaging the actuator 48 withdraws at least a portion of fluid delivery portion 50 from discharge member 44, creating a pressure drop in discharge member 44 relative to reservoir 36 causing fluid to move from reservoir 36 to discharge member 44 through tubing 42. The one-way valves 46, 46' ensure that fluid moves in the desired flow path.

Of course fluid delivery portion 50 of actuator 48 may be coupled to reservoir 36 in any manner suitable to deliver fluid from reservoir 36 to needle lumen 38, sheath lumen 40, and/or passageway 22 when actuator 48 is engaged. For example, fluid delivery portion 50 of actuator 48 may increase pressure in reservoir 36, when actuator 48 is engaged, to force fluid to flow from reservoir 36 through tubing 22, 22' to needle lumen 38, sheath lumen 40, and/or passageway 22. By way of further example, fluid delivery portion 50 of actuator 48 may compress reservoir 36 or a fluid containing portion thereof when the actuator is engaged. Alternatively, reservoir 36, or fluid containing portion thereof, may be placed under pressure by a reservoir biasing element (not shown) or pump (not shown) and fluid delivery portion 50 of actuator 48 may be operatively coupled to a valve that allows pressurized fluid to flow from reservoir 36 to tubing 22, 22', needle lumen 38, sheath lumen 40, and/or passageway 22 when actuator 48 is engaged but prevents flow when actuator 48 is disengaged (see, e.g. FIG. 13). Similarly, fluid may be supplied from an external source (not shown) under, e.g., constant pressure, and reservoir 36 may be omitted. In such embodiments, discharge member 44, may be omitted from the device.

Referring to FIG. 11, an embodiment of the invention where fluid delivery portion 50 of actuator 50 is coupled to reservoir in a syringe-like fashion is shown. Reservoir 36 is fluidly coupled to discharge member 44 through tubing 42. A one-way valve 46 is disposed in tubing 42 between reservoir 36 and discharge member 44. One-way valve 46 allows fluid to flow from reservoir 36 to discharge member 44, but prevents fluid from flowing from discharge member 44 to reservoir 36. Fluid delivery portion 50 of actuator 48 is slidably disposed within discharge member 44. Preferably, fluid delivery portion 50 is disposed in discharge member 44 in a fluid tight manner. A fluid delivery portion 50, or a portion thereof, may have an outer diameter substantially similar to an inner diameter of a portion of discharge member 44 through which fluid delivery portion 50 of actuator 48 slides. Discharge member 44 is fluidly coupled to a lumen, e.g. needle lumen 38, sheath lumen 40, and/or passageway 22, via tubing 42'. A one-way valve 46' may be disposed between in tubing 42' between reservoir 36 and lumen (e.g., 38, 40, 22). One-way valve 46' allows fluid to flow from reservoir 36 to lumen (e.g., 38, 40, 22) but prevents flow from lumen (e.g., 38, 40, 22) to reservoir 36.

Figure 11A:
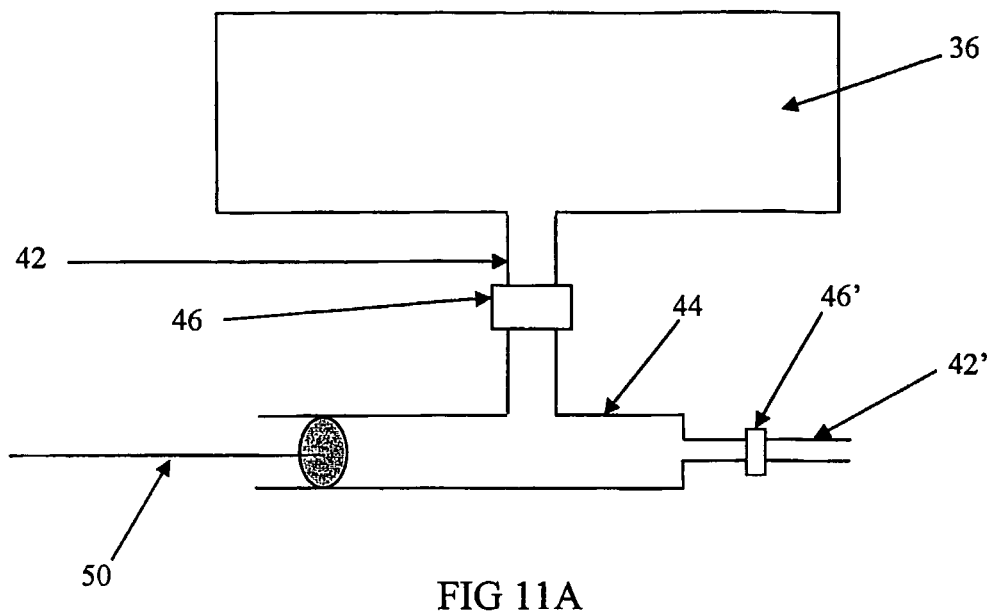
FIGS. 11A and 11B is a diagrammatic illustration of a perspective view of a portion of a device according to an embodiment of the invention.
Figure 11B:
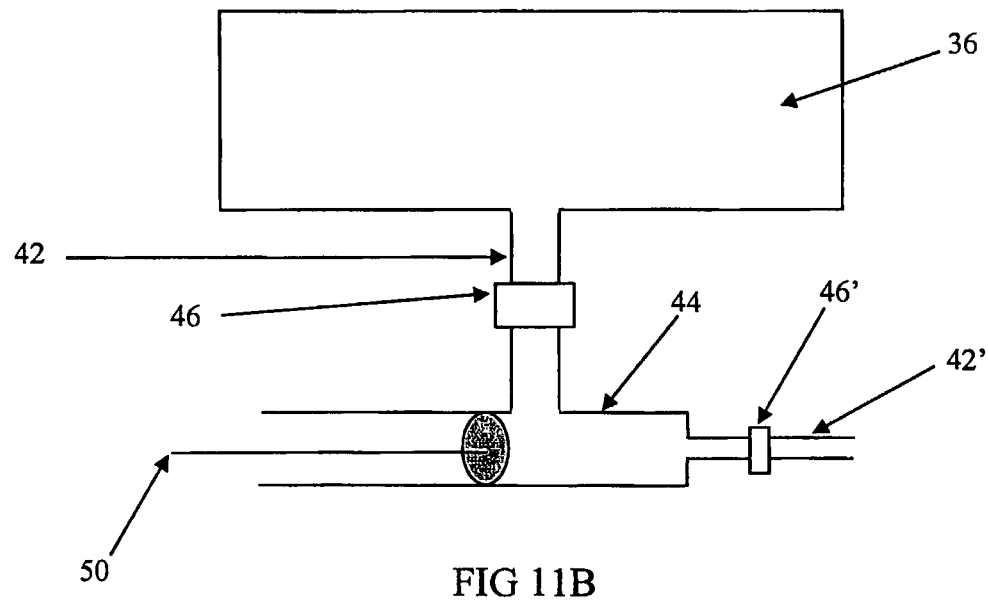

In FIG. 11A, actuator 48 is engaged. The process of engaging the actuator 48 causes fluid delivery portion 50 of actuator 48 to slide through discharge member 44 to cause fluid in discharge member 44 to be discharged through tubing 42' to lumen (e.g., 38, 40, 22). In FIG. 11B, the actuator 48 is disengaged. The process of disengaging the actuator 48 causes the fluid delivery portion 50 of the actuator 48 to slide through discharge member 44, reducing pressure in discharge member 44 relative to reservoir 36 such that fluid flows from reservoir 36 into discharge member 44. Accordingly, fluid for a subsequent lesion will be present in discharge member 44 and prepared for discharge upon subsequent engagement of actuator 48. It should also be understood that, depending on the configuration of reservoir 36 and discharge member 44 within device 10, gravity may assist in causing fluid to flow from reservoir 36 to discharge member 44 when actuator 48 is disengaged or in the process of being disengaged.

Figure 12A:
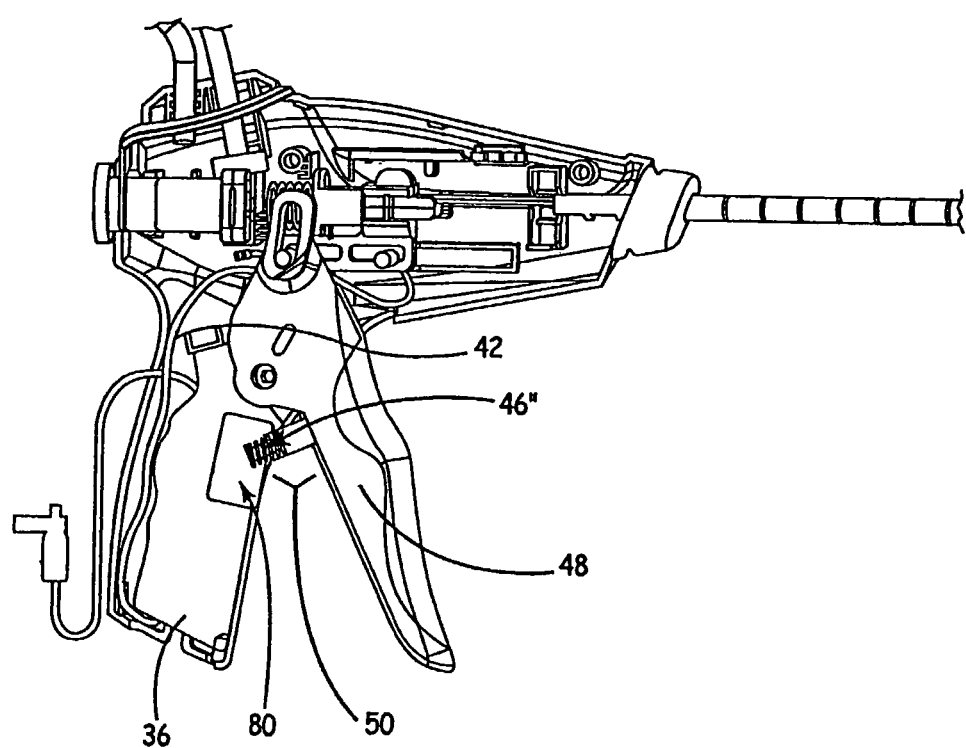
FIGS. 12A and 12B is a diagrammatic illustration of a partially exposed view of a device according to an embodiment of the invention.
Figure 12B:
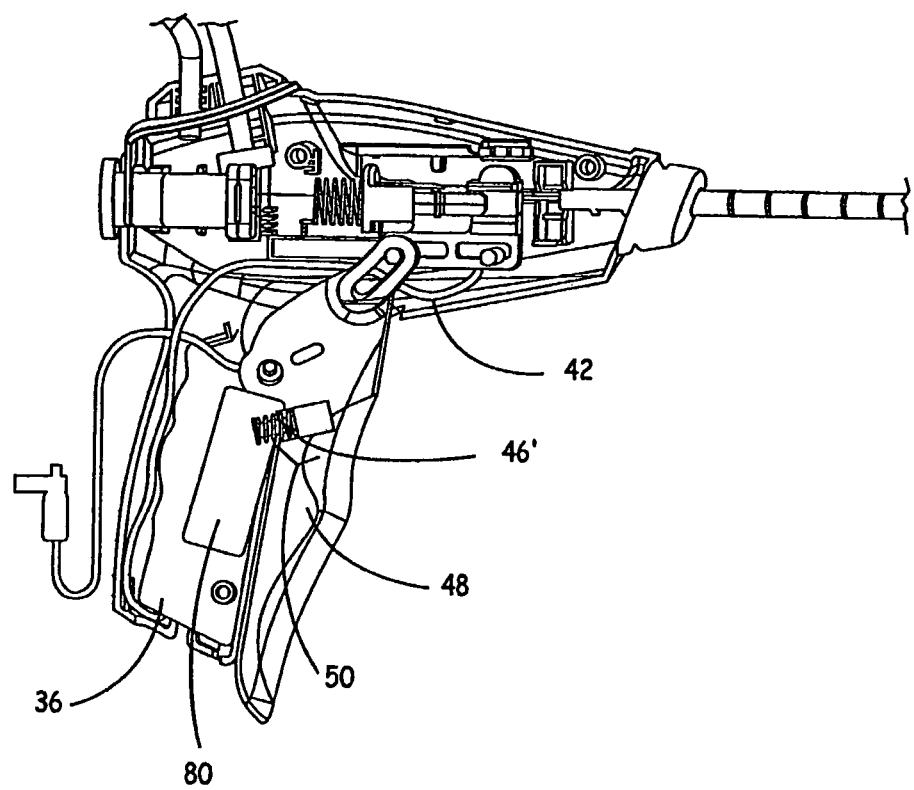

In an embodiment, the reservoir 36 may comprise an expandable bladder 80 that pressurizes fluid to be delivered from device 10. In the embodiment shown in FIG. 12, bladder 80 is disposed within reservoir 36. Bladder 80 is in fluid communication with external environment of device 10 through one-way valve 46". One way valve 46" allows air to flow from outside bladder 80 into bladder 80, but prevents flow of air from inside bladder 80 to outside bladder 80. Fluid delivery portion 50 of actuator 48 is coupled to bladder 80, such that the process of engaging actuator 48 (actuator shown engaged in FIG. 12B an disengaged in FIG. 12A) forces air into expandable bladder 80 causing bladder to expand. As bladder 80 expands, fluid is forced from reservoir 36 through tubing 42 through lumen (e.g., 38, 40, 22).

Figure 13C:
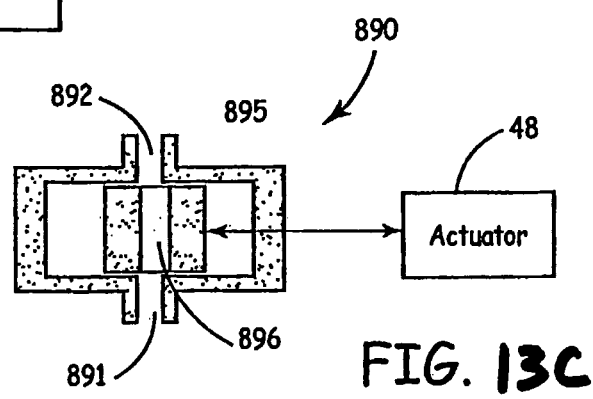

Alternatively and as shown in FIG. 13A, actuator 48 may be coupled to valve 890 disposed in tubing 42, bladder 80 may be expanded, and fluid in reservoir 36 may be pressurized prior to engaging actuator 48, such that engaging actuator 48 opens valve 890 to allow fluid to flow through valve 890. Reservoir 36 may come pre-packaged with an expanded bladder 80 and pressurized fluid. Alternatively, bladder 80 may be expanded prior to use through a separate trigger, pump, etc. mechanism (not shown). In the embodiment depicted in FIG. 13, tubing 42 may be connected to inlet 891 and outlet 892 of valve 890. Valve 890 in FIG. 13 includes a valve core 895 with a bore 896. In FIG. 13C, the valve core 895 is positioned such that fluid moving into the valve 890 through the inlet 891 can flow to the outlet 892 after passing through the bore 896, and corresponds to actuator 48 being engaged. In FIG. 13B, valve 890 is in a closed position such that fluid may not flow through valve 890, corresponding to actuator 46 being disengaged. Sealing between the valve core 895 and the valve body may be by any suitable technique. In some instances, close tolerances in the valve 890 and the viscosity of the fluids being used may be sufficient. In other instances, it may be desirable to use grease, o-rings, gaskets, etc. to provide sealing that prevents or reduces unwanted flow through the valve 890. The valve 890 shown in FIG. 13 is a linear valve in which transitional movement of valve core 895 by actuator 46 changes the valve between an open position (FIG. 13C), in which actuator is engaged, and a closed position (FIG. 13B), in which actuator is disengaged. However, it will be understood that any suitable valve 890 may be used. Further, it will be understood that a reservoir 36 may not be present in a device 10 where actuator 48 is coupled to a valve 890, and that fluid may be supplied from a source outside of device 10, such as, e.g., an external pump (not shown), as shown in e.g. FIG. 14.

Figure 14A:
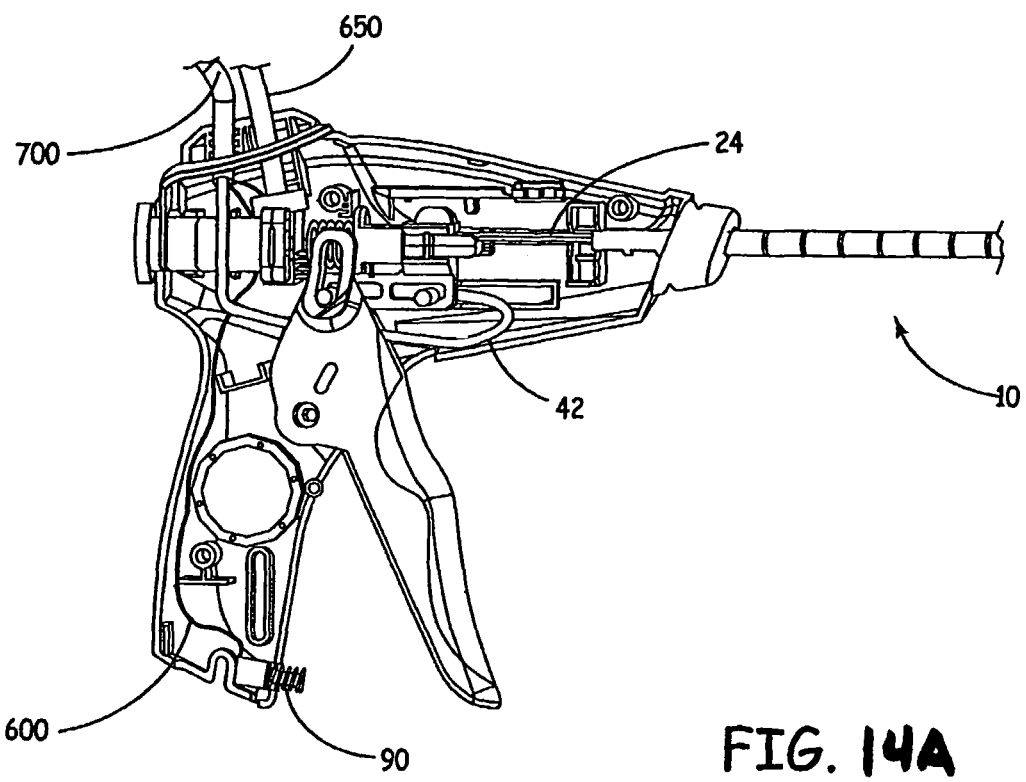
FIGS. 14A and 14B is a diagrammatic illustration of a partially exposed view of a device according to an embodiment of the invention.
Figure 14B:
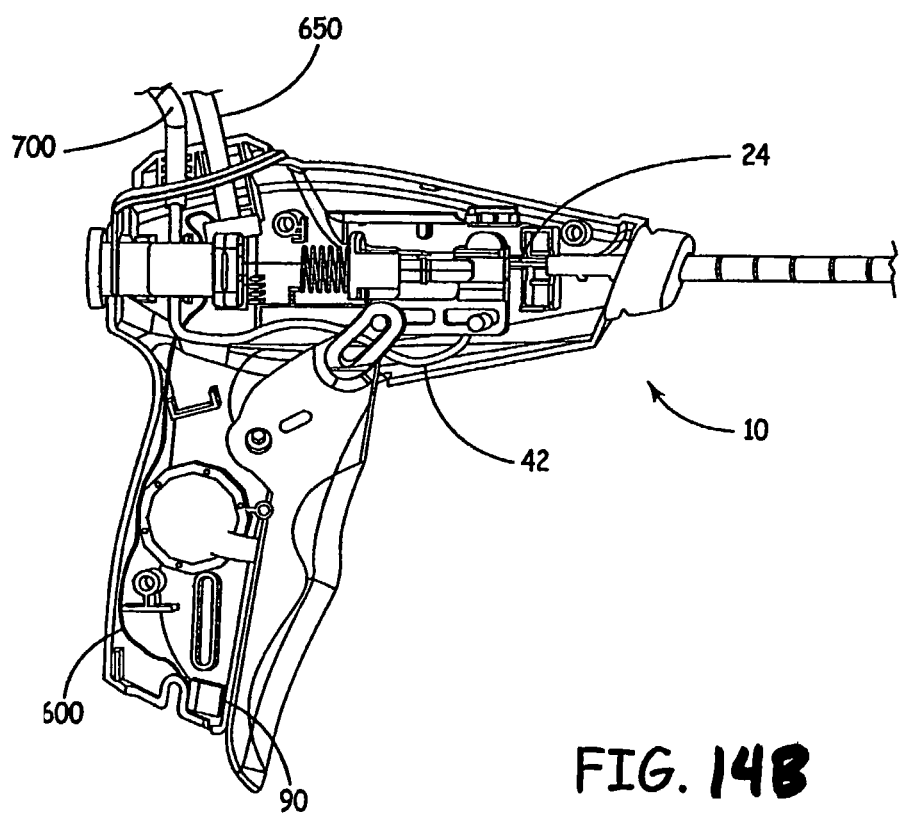
Figure 15A:
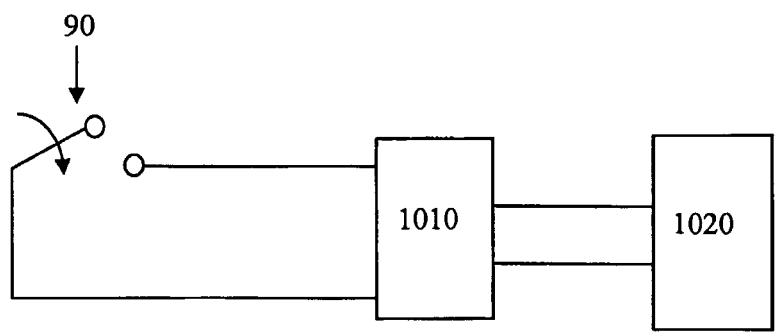
FIGS. 15A and 15B is block diagram of a circuit according to an embodiment of the invention.
Figure 15B:
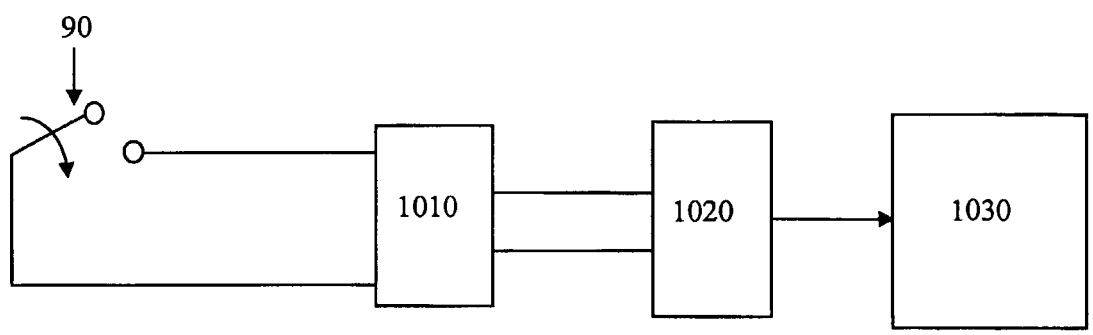

FIG. 14 shows a device 10 comprising a switch 90, such as an electrical contact. Switch 90 is operably coupled to conductor 600, such as a cable or wire. Conductor 600 is shown as being coupled to cable 650, which is operably coupled to an energy source 990 (not shown) external to device. Cable 650 may also be operably coupled to a pump (not shown) containing a reservoir 36, which may be external to device 10. Engaging actuator 48 activates switch 90, e.g. depresses electrical contact, to complete circuit such that energy from energy source 990 (not shown) is applied to needle 24. Actuator 48 of device 10 shown in FIG. 14A is disengaged and actuator 48 shown in FIG. 14B is engaged. Activating switch 90 may also complete a circuit allowing energy to be supplied to a pump (not shown). Pump may contain a reservoir 360 from which fluid may be pumped through external tubing 700 into tubing 42 within device to lumen (e.g., 38, 40, 22). Thus, ablative energy may be applied to needle 42 and fluid may be delivered to target tissue through a single action, namely engaging actuator 48. As discussed below, needle 24 may also be deployed by engaging actuator 48

Needle delivery portion 52 of actuator 48 is coupled to proximal end 26 of needle 24 and is adapted to cause the distal portion of the needle to extend into a target tissue. In the embodiment shown in e.g. FIG. 6 needle delivery portion 52 of actuator 48 may be coupled to block 64, which is coupled to proximal end 26 of needle 24. As shown in, e.g., FIG. 6, block 64 is slidably mounted in block guiding member 66 of housing 12. Block 64 comprises extensions 68. Block guiding member 66 is configured to receive extension 68 of block 64. Actuator 48 comprises block extension receiver 70, which is configured to receive extension 68 of block 64. When actuator 48 is engaged (e.g. FIG. 7), block 64 slides within housing 12 causing needle to slide through passageway 22 of elongate probe member 14. When actuator 48 is fully engaged (e.g. FIG. 7), distal end 28 of needle exits opening 72 of elongate probe member 14. While not shown in e.g. FIGS. 6-8, it will be understood that sheath 30 may also be coupled to needle delivery portion 52 of actuator 48. Sheath 30 may be coupled to block 64 as shown in e.g. FIG. 6 with regard to needle 24.

Figure 7:
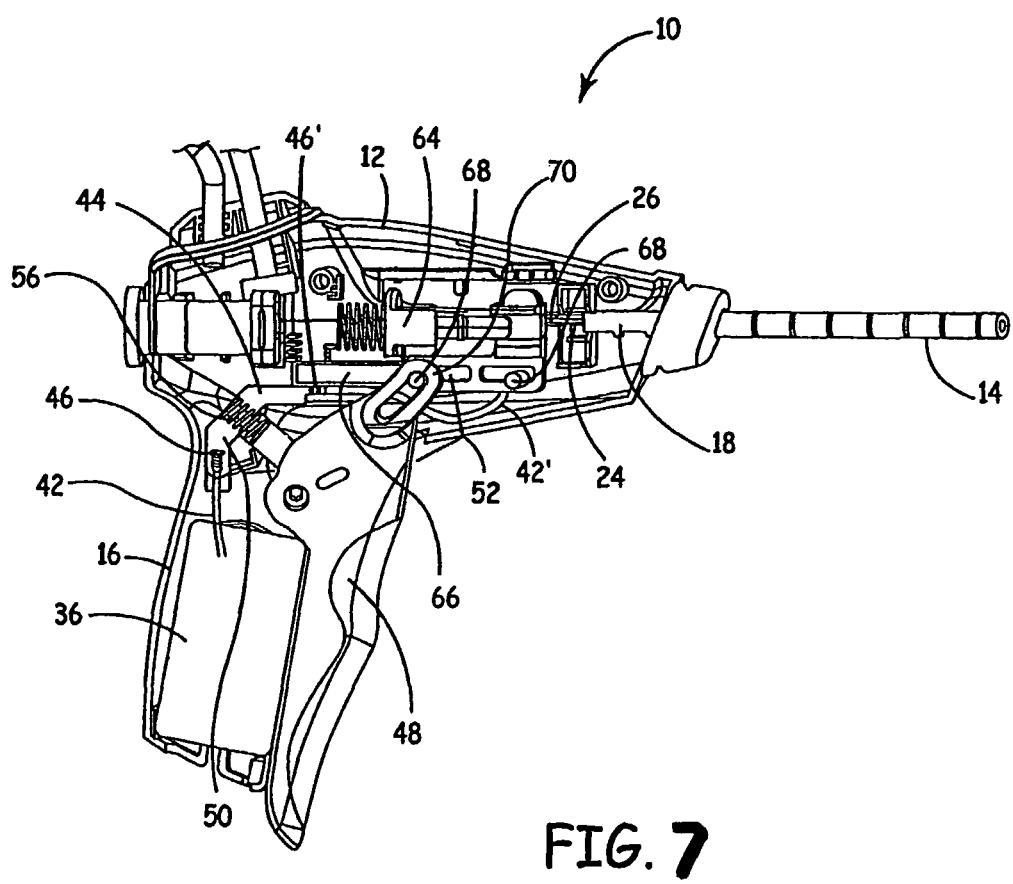
FIG. 7 is a diagrammatic illustration of a view of a partially exposed view of a device as in FIG. 6, wherein the actuator is engaged.

The actuator 48, as shown in e.g. FIG. 6, is disengaged. The actuator, as shown in e.g. FIG. 7, is engaged. Engaging the actuator 48 causes the distal portion of the needle to extend into a target tissue. Engaging the actuator 48, in various embodiments, may also cause fluid to flow through one or more of needle lumen 38, sheath lumen 40, and/or passageway 22 to target tissue location.

Figure 10:
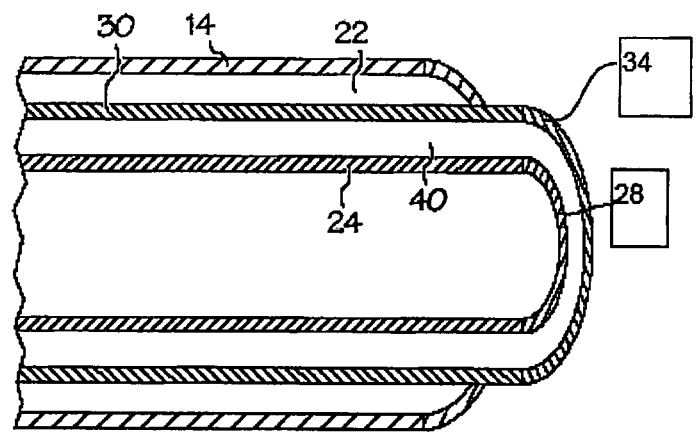
FIG. 10 is a diagrammatic illustration of a longitudinal section of a portion of a device as in FIG. 7.

FIGS. 9 and 10 depict a longitudinal section of elongate probe member 14 corresponding to a section to the right of line 240 in FIG. 6. While FIG. 6 does not depict a sheath 30, FIGS. 9 and 10 do depict a sheath 30, which is slidably disposed within passageway 22 of probe member 14. Needle 24 is slidably disposed within lumen 40 of sheath 30. Referring to FIG. 9, the needle 24 is retracted (i.e., the distal end 28 of needle 24 is within the confines of passageway 22), and the actuator 48 (not shown) is disengaged. Referring to FIG. 10, the needle 24 is deployed (i.e, extending through the opening 72 of passageway 22), and the actuator 48 (not shown) is engaged. As shown in FIGS. 9 and 10, the actuator 48 (not shown) may be coupled to sheath 30 and be adapted to cause the distal end 34 of sheath 30 to extend through the opening 72 of passageway 22 into a target tissue. The sheath 40 may be at least partially retracted (not shown) prior to applying ablative energy to the tissue location via the needle electrode 24. The one or more needle electrodes 24 may be coupled to an energy source 990 (not shown), such as an RF generator, such that ablative energy may be applied to the tissue through the needle 24.

Figure 16:
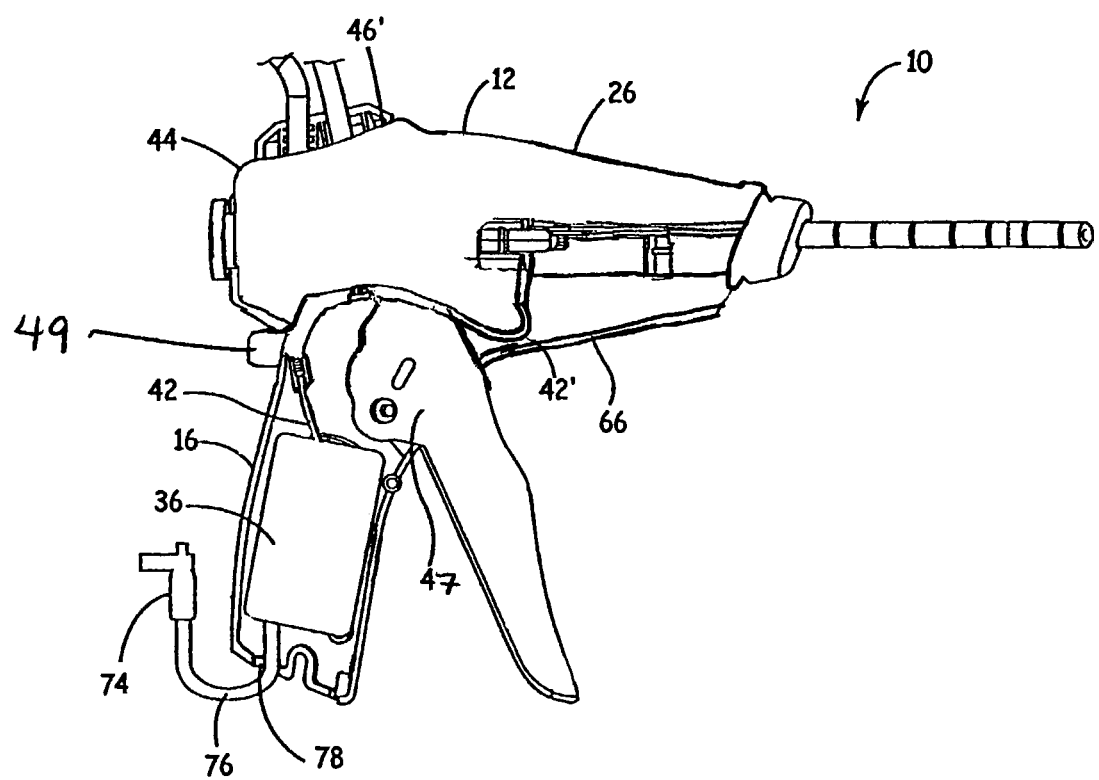
FIG. 16 is a diagrammatic illustration of a partially exposed view of a device according to an embodiment of the invention.

FIG. 16 depicts a simplified version of one embodiment of a device of the invention. The device depicted in FIG. 16 is simplified and may not depict all components. It should be understood by one of skill in the art, that the components of a device of this invention can be similar to those discussed above. The embodiment depicted in FIG. 16 includes an electrode actuator 47 and a fluid actuator 49, contrary to the embodiments depicted in FIGS. 6, 7, 12, 13, and 14, which included an actuator 48 that activated both the electrode 900 and the reservoir 36. Embodiments that include both an electrode actuator 47 and a fluid actuator 49 can be configured to operate similar to those depicted in FIGS. 6, 7, 12, 13, and 14. For example, the fluid actuator 49 can utilize a biasing element, similar to biasing element 56 depicted in FIG. 6; a syringe-like configuration, similar to FIG. 7; a bladder like configuration similar to FIG. 12; a valve configuration similar to FIG. 13; or an actuator that activates a switch to complete a circuit to power a pump system similar to FIG. 14.

The electrode actuator 47 can be configured to function similar to the actuator 48 discussed with respect to FIGS. 6, 7, 12, 13, and 14. For example, a block can be slidably mounted in a guiding member of the housing of the device that slides within the housing causing the needle to slide through a passageway of the probe member as discussed with respect to FIGS. 6 and 7.

Numerous functional configurations of both the electrode actuator 47 and the fluid actuator 49 were discussed above and with respect to the independent functions of the actuator 48. There are also numerous ways of configuring the fluid actuator 49 and the electrode actuator 47 that can be utilized in embodiments of the invention. The configuration of the electrode actuator 47 and the fluid actuator 49 depicted in FIG. 16 are only one example of configurations that can be utilized in embodiments of the invention. In FIG. 16, the electrode actuator 47 is depicted as a trigger like mechanism, however, one of skill in the art, having read this specification will understand that other configurations that can activate a functional component such as the block assembly discussed above or other comparable functional methods of activating the electrode 900, can be utilized in embodiments of the invention. For example, the electrode actuator 47 may be in the form of a button, slide, switch, trigger, or any other means capable of causing an electrode to be introduced into a target location.

The configuration of the fluid actuator 49 can also vary, as would be known to one of skill in the art, having read this specification. In FIG. 16 the fluid actuator 49 is a button that for example could be pressed to turn the fluid flow on and off. One of skill in the art, having read this specification will understand that other configurations that can activate functional components discussed above or other comparable functional methods of causing fluid to flow from the reservoir 36 to the target location can be utilized in embodiments of the invention. For example, the fluid actuator 49 may be in the form of a button, slide, switch, trigger, plunger like mechanism, squeeze type actuator that could apply pressure to a bladder like system, or any other means capable of causing fluid to flow from the reservoir 36 to the target tissue location.

The electrode actuator 47 and the fluid actuator 49 are depicted in FIG. 16 in particular positions on the housing 12 of the device 10. It should be understood by one of skill in the art, having read this specification, that the electrode actuator 47 and the fluid actuator 49 can be located at numerous positions on the housing 12 of the device 10. In one embodiment, the position of the electrode actuator 47 and the fluid actuator 49 are chosen with ease and comfort of physician use in mind. In another embodiment, the electrode actuator 47 and the fluid actuator 49 are purposefully placed at distant locations on the housing 12 of the device 10, in order to minimize the possibility of confusion during use. In one embodiment, the electrode actuator 47 is on the front of the handle 16 (the side of the handle 16 closest to the elongate probe member 14) and the fluid actuator 49 is on the back of the handle 16. In another embodiment, the electrode actuator 47 is on the front of the handle 16 and the fluid actuator 49 is on the top of the housing 12 (the surface opposite the handle 16). In yet another embodiment, the fluid actuator 49 is located on one side of the handle 16 and the electrode actuator 47 is on the front of the handle 16.

Any medically acceptable conductive fluid may be delivered from device 10 to the target tissue location. As used herein, "conductive fluid" means a fluid capable of increasing conductivity of a tissue in which the fluid is placed. For example, a conductive fluid may be a solution comprising an ion capable of enhancing the conductivity of a tissue. The solution may comprise a cation having a charge of, e.g., +1 to +3 and/or may comprise an anion having a charge of, e.g., −1 to −3. A conductive fluid may be a solution comprising a salt. Any medically acceptable salt may be employed according to various embodiments of the invention. By way of example, a suitable salt may comprise sodium, potassium, calcium, and/or magnesium as a potential cation and may contain chloride, nitrate, nitrite, sulfate, phosphate, sulfate, and/or carbonate as a potential anion. The salts may be monobasic, dibasic, tribasic, etc. Specific exemplary salts include $NaCl$, $CaCl_2$, $MgCl_3$, $KMgCl_3$, $Na_2SO_3$, $CaSO_4$, $MgSO_4$, $Na_2HPO_4$, $Ca_{10}(PO_4)_6$, $Mg_3(PO_4)_2$, $NaHCO_3$, $CaCO_3$, $MgCO_3$, $CaMgCO_3$, $NaNO_3$, $NaNO_2$, $KCl$, $KNO_3$, and $KNO_2$. Reference to a salt herein is intended to refer to anhydrous and hydrated forms of the salt. The conductive fluid may also include pharmaceutical agents. Examples of pharmaceutical agents that can be added to the conductive fluid include, but are not limited to, anesthetic agents, steroids, and vaso-constrictors.

A conductive fluid may comprise any concentration of a salt capable of increasing conductivity of a tissue in which the fluid is placed. In an embodiment, the conductive fluid comprises a salt concentration of about 0.9% by weight or greater. In an embodiment the conductive comprises a salt concentration of between about 0.9% and about 35% by weight.

Any amount of conductive fluid capable of increasing the conductivity of a target tissue may be delivered from device 10 to target tissue. In an embodiment, greater than about 0.1 cc of conductive fluid is delivered. In an embodiment, between about 0.1 cc to about 5 cc of conductive fluid is delivered.

An embodiment of the invention provides a method for ablating tissue at a target location. The method comprises introducing an electrode into the target location and introducing a conductive fluid to the target location. As used herein, "target location" means tissue to be ablated and tissue in proximity to the tissue to be ablated. In one embodiment, the electrode and the conductive fluid are introduced into the target location through a single step carried out by a user of a system capable of introducing the electrode and the conductive fluid. The method further comprises applying energy to the target location via the electrode to ablate the tissue.

In such an embodiment, the single step of introducing the electrode and the conductive fluid may comprise engaging an actuator 48, as e.g. described above. The actuator 48 may be in the form of a trigger capable of being pulled by a human hand, as e.g. described above. Alternatively, the actuator may be in the form of a button, slide, switch, or any other means capable of causing an electrode to be introduced into a target location and capable of causing conductive fluid to be delivered to the target location. The actuator 48 may be operatively coupled to the electrode 24 and a supply housing the conductive fluid. The supply may be a reservoir 36, as e.g. described above. In an embodiment, a needle 24 comprises the electrode and the electrode is introduced by moving the needle.

In an embodiment, engaging the actuator causes the needle to be introduced to the target location and causes conductive fluid to flow from a supply housing the conductive fluid to the target location. Any means for causing the conductive fluid to flow from the supply to the target location may be employed. In an embodiment, engaging the actuator increases pressure in a supply housing the conductive fluid, forcing the conductive fluid to be discharged from the supply and directed to a target location. In an embodiment, engaging the actuator decreases pressure upstream the supply housing the conductive fluid, relative to the supply, causing the conductive fluid to be drawn from the supply towards the target location. In an embodiment, engaging the actuator opens a valve allowing the conductive fluid to flow to the target location. The valve is in fluid communication with the source of conductive fluid and has an open position and a closed position. The open position allows flow of the conductive fluid to the target tissue and the closed position prevents flow of the conductive fluid to the target tissue. The conductive fluid may be delivered under substantially constant pressure and/or at a substantially constant rate, such as when delivered by a pump.

Another embodiment of the invention includes a method for ablating tissue at a target tissue location and introducing a conductive fluid to the target tissue location in more than one step. The more than one step of introducing the electrode and the conductive fluid is carried out by a user of a system capable of introducing the needle and the conductive fluid. The method further comprises applying energy to the target tissue location via the electrode to ablate the tissue.

Devices 10 according to the teachings of various embodiments of the invention may be used to ablate any tissue in a subject, such as a human patient, in need thereof. For example, prostate tissue may be ablated, tumors may be ablated, cardiac tissue may be ablated, skin tissue, kidney tissue, bladder tissue including tissue of the bladder neck, etc. Accordingly, various diseases or disorders may be treated using a device 10 capable of delivering a conductive fluid to a target tissue and extending needle electrodes 24 to a target tissue in a single action according to the teachings of various embodiments of the invention. In general, any disease or disorder of a subject that may benefit from ablation of a tissue may be treated. For example, hyperplasia, such as benign prostatic hyperplasia, stress incontinence, skin wrinkles, or cancer may be treated.

Various embodiments of the invention are disclosed. One skilled in the art will appreciate that embodiments other than those disclosed are contemplated. One of skill in the art will also appreciate that one or more element of one or more embodiments described herein may be combined to produce an apparatus or method in accordance with the teachings disclosed herein. The disclosed embodiments are presented for purposes of illustration and not limitation, and the present invention is limited only by the claims that follow.

All printed publications, such as patents, patent applications, technical papers, and brochures, cited herein are hereby incorporated by reference herein, each in its respective entirety.

What is claimed is:

1. A device for ablating a target tissue, comprising:
a housing;
an electrode slidably disposed within the housing;
a reservoir capable of housing a conductive fluid;
an electrode actuator operably coupled to the electrode, the electrode actuator being configured to cause the electrode to extend into the target tissue from the housing; and
a fluid actuator operably coupled to the reservoir, the fluid actuator being configured to cause the fluid to flow from the reservoir to the target tissue;
a fluid lumen, in fluid communication with the reservoir configured to deliver the fluid to the target tissue;
a valve having an inlet and an outlet, the inlet being in fluid communication with the reservoir, the outlet being in fluid communication with the fluid lumen; being configured to move between an open position and a closed position, the open position allowing fluid to flow from the inlet to the outlet, the closed position preventing fluid to flow from the inlet to the outlet; being coupled to the fluid actuator such that engaging the fluid actuator moves the valve to the open position and such that disengaging the fluid actuator moves the valve to the closed position; and
a bladder disposed in the reservoir; and capable of being expanded, wherein the bladder pressurizes fluid within the reservoir when the bladder is expanded.

2. The device of claim 1, wherein the electrode is an ablation needle.

3. The device of claim 2, wherein the fluid lumen is a lumen of the ablation needle.

4. The device of claim 2, further comprising a sheath, the sheath:
disposed within the housing; and
comprising a sheath lumen, the needle being slidably disposed within the sheath lumen.

5. The device of claim 4, wherein the fluid lumen is within the sheath and outside of the ablation needle.

6. The device of claim 2, further comprising a passageway formed within the housing.

7. The device of claim 6, wherein the passageway is the fluid lumen.

8. The device of claim 7, wherein the electrode is an ablation needle, the needle
being slidably disposed within the passageway, and
comprising a needle lumen,
wherein the fluid lumen is at least one of the passageway and Of the needle lumen.

9. The device of claim 8, further comprising a sheath, the sheath:
disposed within the housing; and
comprising a sheath lumen, the needle being slidably disposed within the sheath lumen,
wherein the fluid lumen is at least one of the passageway, the sheath lumen, and the needle lumen.

10. The device of claim 1, further comprising a discharge member, the discharge member:
comprising proximal and distal portions,
the proximal portion of the discharge member being in fluid communication with the reservoir,
the distal portion of the discharge member being in fluid communication with the fluid lumen;
being coupled to the fluid actuator and configured
such that engaging the fluid actuator causes the conductive fluid to flow through the fluid lumen from the discharge member to the target tissue and such that disengaging the fluid actuator causes the conductive fluid to flow from the reservoir to the discharge member.

11. The device of claim 10, further comprising a first one-way valve and a second one-way valve,
the first one-way valve coupled to the reservoir and the discharge member and configured to allow fluid to flow from the reservoir to the discharge member,
the second one-way valve coupled to the discharge member and the fluid lumen and configured to allow fluid to flow from the discharge member to the fluid lumen.

12. The device of claim 1, wherein the fluid actuator is coupled to the bladder, such that engaging the fluid actuator expands the bladder.

13. The device of claim 12, further comprising a one-way valve coupled to the fluid actuator and the bladder, the one-way valve configured to allow fluid to enter the bladder.

14. A system for ablating a target tissue, comprising
a device according to claim 1; and
an energy source for ablating the target tissue operably coupled to the electrode.

15. The system of claim 14, wherein:
the electrode actuator is operably coupled to the energy source; and
the electrode actuator is configured to cause the energy source to deliver ablative energy to the target tissue via the electrode.

16. The system of claim 15, wherein the electrode actuator is configured to, in a single step of actuating the electrode actuator, cause the electrode to extend into the target tissue from the housing and cause the energy source to deliver ablative energy to the target tissue via the electrode.

17. The device of claim 1, wherein the housing comprises the reservoir and the bladder, and wherein the bladder is disposed in the reservoir.

18. The device of claim 1, wherein the housing comprises a handle portion extending therefrom, and wherein the reservoir is disposed at least partially within the handle portion.

19. The device of claim 1, wherein:
the electrode actuator is operably coupled to an energy source;
the energy source is operably coupled to the electrode; and
the electrode actuator is configured to cause the energy source to deliver ablative energy to the target tissue via the electrode.

20. The device of claim 19, wherein the electrode actuator is configured to, in a single step of actuating the electrode actuator, cause the electrode to extend into the target tissue from the housing and cause the energy source to deliver ablative energy to the target tissue via the electrode.

21. A device for ablating a target tissue, the device comprising:
a housing;
an electrode slidably disposed within the housing;
a reservoir configured to house a conductive fluid;
an electrode actuator operably coupled to the electrode, the electrode actuator being configured to cause the electrode to extend into the target tissue from the housing;
a fluid actuator operably coupled to the reservoir, the fluid actuator being configured to cause the fluid to flow from the reservoir to the target tissue;
a fluid lumen, in fluid communication with the reservoir and configured to deliver the fluid to the target tissue;
a bladder disposed in the reservoir and configured to be expanded, wherein the bladder pressurizes fluid within the reservoir when the bladder is expanded;

a discharge member, the discharge member:
- comprising proximal and distal portions,
  - the proximal portion of the discharge member being in fluid communication with the reservoir,
  - the distal portion of the discharge member being in fluid communication with the fluid lumen; and
- coupled to the fluid actuator and configured
  - such that engaging the fluid actuator causes the conductive fluid to flow through the fluid lumen from the discharge member to the target tissue and
  - such that disengaging the fluid actuator causes the conductive fluid to flow from the reservoir to the discharge member; and a first one-way valve and a second one-way valve,
- the first one-way valve coupled to the reservoir and the discharge member and configured to allow fluid to flow from the reservoir to the discharge member,
- the second one-way valve coupled to the discharge member and the fluid lumen and configured to allow fluid to flow from the discharge member to the fluid lumen.

\* \* \* \* \*